(12) United States Patent
Rappuoli et al.

(10) Patent No.: US 6,403,099 B1
(45) Date of Patent: Jun. 11, 2002

(54) CONJUGATES FORMED FROM HEAT SHOCK PROTEINS AND OLIGO-OR POLYSACCHARIDES

(75) Inventors: Rino Rappuoli, Quercegrossa; Paolo Costantino, Colle d'Elsa; Stefano Viti, Sovicille; Francesco Norelli, Siena, all of (IT)

(73) Assignee: Chiron S.p.A., Siena (IT)

(*) Notice: Subject to any disclaimer, the term of this patent is extended or adjusted under 35 U.S.C. 154(b) by 0 days.

(21) Appl. No.: 08/256,847

(22) PCT Filed: Mar. 8, 1993

(86) PCT No.: PCT/EP93/00516

§ 371 (c)(1),
(2), (4) Date: Nov. 1, 1994

(87) PCT Pub. No.: WO93/17712

PCT Pub. Date: Sep. 16, 1993

(30) Foreign Application Priority Data

Mar. 6, 1992 (IT) .......................................... FI92A0058

(51) Int. Cl.⁷ ...................... C01B 3/00; G01N 33/554; C07K 1/00

(52) U.S. Cl. .............................. 424/248.1; 424/192.1; 530/395; 514/569; 435/7.32; 435/12

(58) Field of Search ................................. 424/92, 194.1, 424/248.1; 530/395; 514/569; 435/7, 7.32, 12

(56) References Cited

U.S. PATENT DOCUMENTS

| | | | | |
|---|---|---|---|---|
| 4,356,170 A | * | 10/1982 | Jennings ........................ | 424/92 |
| 4,529,602 A | * | 7/1985 | Wada et al. ................... | 514/569 |
| 4,707,543 A | * | 11/1987 | Zollinger et al. ............. | 530/402 |
| 4,711,779 A | * | 12/1987 | Porro et al. .................... | 424/92 |
| 4,727,136 A | * | 2/1988 | Jennings ........................ | 530/395 |
| 4,748,113 A | * | 5/1988 | Marshall ........................ | 435/12 |
| 4,882,271 A | * | 11/1989 | Evans et al. .................... | 435/7 |
| 4,965,192 A | * | 10/1990 | Maes ............................... | 435/7 |
| 5,200,344 A | * | 4/1993 | Blaser et al. ................... | 435/7.32 |
| 5,370,872 A | * | 12/1994 | Cryz et al. ..................... | 424/194.1 |
| 5,468,481 A | * | 11/1995 | Sharma ........................... | 424/282.1 |
| 5,591,632 A | * | 1/1997 | O'Donnell et al. ............ | 435/252.3 |
| 5,599,545 A | * | 2/1997 | Stanford et al. ............... | 424/282.1 |
| 5,651,971 A | * | 7/1997 | Lees ............................... | 424/194.1 |
| 5,736,146 A | * | 4/1998 | Cohen et al. ................... | 424/194.11 |
| 5,843,460 A | * | 12/1998 | Labigne et al. ................ | 424/234.1 |
| 6,077,706 A | * | 6/2000 | Covacci .......................... | 435/325 |

FOREIGN PATENT DOCUMENTS

| | | | | |
|---|---|---|---|---|
| EP | 0329570 | * | 8/1989 | ......... G01N/33/569 |
| EP | 429816 A | * | 6/1991 | |
| WO | 8908843 | * | 9/1989 | .......... G01N/33/53 |
| WO | 9216232 | * | 1/1992 | ......... A61K/39/385 |
| WO | 9318150 | * | 9/1993 | |

OTHER PUBLICATIONS

Byrd et al, Veterinary Immunology and Immunopathology, vol. 34, pp. 307–324, 1992.*
Young, R.A., Annu. Rev. Immunol., vol. 8, pp. 401–420, especially p. 411, 1990.*
Lussow, A.R. et al, Immunology Letters, vol. 25, pp. 255–264, 1990.*
Del Giudice, G. et al, Res. Immunol. vol. 142, pp. 703–707, 1991.*
Dick, W.E., Jr. et al, Conjugate Vaccines, vol. 0(0), pp. 48–114, 1989.*
Barrios et al, Eur. J. Immunol., vol. 22(6), pp. 1365–1372, 1992.*
Goodwin, CRC Press, Chapter 25, *Helicobacter pylori*, biology and clinical practice, pp. 431–444, 1993.*
Stover, et al, Nature, vol. 351, pp. 456–460, Jun., 1991.*
Schneerson, R et al, Towards Better Carbohydrate Vaccines, pp. 307–327, especially p. 321, 1987.*
Matthews, RC. et al, Immunology, vol. 74, p 20–24, 1991.*
Shinnick T.M. et al, Current Topics in Microbiology and Immunology, vol. 167, p 145–160, 1991.*
Yakota, K. et al, Microbiol. Immunol., vol. 38(5), 1994, p 403–405.*
Bukanov, N.O. et al, Molecular Microbiol, Feb. 1994, vol. 11(3), p 509–523.*
Rapzaeroli, R et al (1993), Gastroenterology and Hepatology, vol. 5 (suppl. 2), p 576–578.*
Ghiara, P et al, Current Opinion in Gastroenterology, 1995, 11(suppl) pp 52–56.*
Verheul, A.F.M. et al, Infection and Immunity, Oct. 1991, p. 3566–3573, vol. 59, No. 10.*
Jennings, Harold, J. of Infectious Diseases, 1992, 165 (Suppl 1): S156–9.*
Insel, R.A. et al, J. Exp. Med., vol. 163, Feb. 1986, p 262–269 Oligosaccharide–Protein conjugate vaccines induce and prime for oligoclonal IgG Antibody Responses to the *Haemophilius influenza* 6 capsular polysaccharide in Human Infants.*

(List continued on next page.)

Primary Examiner—Lynette R. F. Smith
Assistant Examiner—Ginny Allen Portner
(74) Attorney, Agent, or Firm—Gwilym J.O. Attwell; Alisa A. Harbin; Robert P. Blackburn

(57) ABSTRACT

The present invention provides conjugate compounds comprising at least one heat shock protein or portion thereof including at least one immunostimulatory domain and at least one capsular oligosaccharide or polysaccharide of a pathogenic bacteria. The compound comprises oligosaccharides of the Meningococci C (MenC) group and a heat shock protein selected from *M. bovis* BCG GroE1-type 65 kDa hsp (hspR65), recombinant *M. tuberculosis* DnaK-type 70 kDa hsp (hspR70) and a heat shock protein from *H. pylori*. The invention also provides processes for producing conjugate compounds, pharmaceutical compositions comprising conjugate compounds, therapeutic compositions comprising conjugate compounds, and methods of inducing an immune response.

11 Claims, 7 Drawing Sheets

OTHER PUBLICATIONS

Verhuel, A.F.M. et al, Infection & Immunity, Mar. 1991, p 843–851.*

Verhuel, A.F.M et al, Molecular Immunology, 1991, vol. 28, No. 11 p 1193–1200.*

Claesson, B.A. et al., "Clinical and immunologic responses to the capsular polysaccharide of *Haemophilus influenze* type b alone or conjugated to tetanus toxoid in 18– to 23–month–old children", *J. Pediatrics St. Louis*, 1988, 112, 695–702.

Dunn, B.E. et al., "Identification and Purification of a cpn60 Heat Shock Protein Homolog from *Helicobacter pylori*", *Infect. & Immun.*, 1992, 60, 1946–1951.

Ellis, J., "Cytosolic chaperonin confirmed", *Nature*, 1992, 358, 191–192.

Evans, D.J., Jr. et al., "Urease–Associated Heat Shock Protein of *Helicobacter pylori*", *Infect. Immun.*, 1992, 60, 2125–2127.

Lussow, A.R. et al., "Mycobacterial heat–shock proteins as carrier molecules", *Eur. J. Immunol.*, 1991, 21, 2297–2302.

Peeters, C.C.A.M. et al., "Effects of Carrier Priming on Immunogenicity of Saccharide–Protein Conjugate Vaccines", *Infect. & Immun.*, 1991, 59, 3504–3510.

Robbins, J.B. et al., "Polysaccharide–Protein Conjugates: A New Generation of Vaccines", *J. Infect. Dis.*, 1990, 161, 821–832.

* cited by examiner

```
                                                              1                                                      13
1) H.pylori                                                   MAK EIKFSDSARN
2) P.aeruginosa                                               MA.. .V..G....K
3) C.trachomatis                                              MV.. N..YNEE..K
4) M.leprae      VPGRDGETQP ASCGRPSRAL HPASVSNGGC RHPVTLASFL IRRNHFA... T.AYDEE..R
5) H.sapiens                                MLRLPTVF RQMRPVSRVL APHLTRAY.. DV..GAD..A 14                                                                                                                83
1) LLFEGVRQLH DAVKVTMGPR GRNVLIQKSY GAPSITKDGV SVAKEIELSC PVANMGAQLV KEVASKTADA
2) KMLV..NV.A ...A.L..K  ...VLD..F  ...T...... .......... ..KD KFE. ........D. ..RPT...
3) KIQK..KT.A E....L..K  ..H.V.D..F .S.QV..... T....V..AD KHE....... M........K
4) G.ER.LNS.A .......L.K ....VLE.KW ...T..N... .I........ ..ED .YEKI.E... ....K..D.V
5) .MLQ..DL.A ...A......K ..T.I.EQ.W .S.KV..... T...S.D.ED KYK.I.K..  QD..NN.NEE 84                                                                                                               153
1) AGDGTTTATV LAYSIFKEGL RNITAGANPI EVKRGMDKAA EAIINELKKA SKKVGGKEEI TQVATISANS
2) ..QA.VN... KAVAA.M..M DL...I..PT V..VAQ..EL A.PWRDTKA. A...G......
3) ..EA.YT... ..V.......M DL...I....V KVVVDQI..I ..P.QHHK.. A........N
4) ..QALV.... ..VA.....L GL...IE..V DKVTET.L.D A.E.ET..Q. AAT.A...-G
5) ..R..A...F EK.SK....V .IR..VML.V D.V.A....Q ..P.TTP... A.........G
```

FIG. 2(a)

```
     154
1)   DHNIGKLIAD AMEKVGKDGV ITVEEAKGIE DELDVVEGMQ FDRGYLSPYF VTNAEKMTAQ LDNAYILLTD
2)   ..ES..QI..E .........E ......GS.L N..S..... .......... .........  ..NKPDT.A.E ..SPLL..V.
3)   ..AE..N...E .........  .........  .....TV... .N........ A..P.TQECV .ED.LV.IY.
4)   ..QS..D...E ...D...NE. .....SNTFG LQ.ELT....R .....K..I.G.. ..D..RQE.V .EEP....VS
5)   ..KE..NI.S. ...K...RK..   .....KDG.TLN ...EII...K .......I..  INTSKGQKCE FQD..V..SE 224                                                                        293
1)   KKISSMKDIL PLLEKTMKEG KPLLIIAEDI EGEALTTLVV NKLRGVLNIA AVKAPGFGDR RKEMLKDIAI
2)   ....NIREM. .V..AVA.A. R.....V...V  .........A  .NM..IVKV. .........  ...A..Q...
3)   ....GI..F. .I..QQVAES. R.........  .........A  .RI..GFRVC .........  ...A..E...
4)   .S.V.TV..L .....VIQA.  .........S  .........V  .I..TFKSV  .........  ...A..Q.M.
5)   .......... .IQS.V .A..IANAHR .......V  .........D  .....S...L .R.KVG.QVV  ...NQ...M..

294                                                                        362
1)   LTGGQVISEE -LGLSLENAE VEFLGKAGRI VIDKDNTTIV DGKGHSDDVK DRVAQIKTQI ASTTSDYDKE
2)   ....T..... -V.....G.T L.H...PK.V ..N.E....I ..A.VQA.IE A..L..RK..  EE......R.
3)   ....L..... -...MK....N LAM....KKV IVS.ED..... E.M.EKEALE A.CES..K..  EDSS......
4)   .-V..T....TD LSL....RKV .MT..E.... E.A.DT.AIA G....R.E. ENSD......R.
5)   A...A.FG.. G.T.N..DVQ PHD...V.EV IVT..DAMLL K...DKAQIE K.IQE.IE.L DV...E.E..
```

FIG. 2(b)

```
     363
1)   KLQERLAKLS GGVAVIKVGA ASEVEMKEKK DRVDDALSAT KAAVEEGIVI GGGAALIRAA QKVH--LNL-    429
2)   .......... .......... .T........ AP.E...H.. R.......V.P ...V..V..L .AIEG..KGD
3)   .......... .......R.. .T.I...... ......QH.. I.........T....CI PTLEAF.PML
4)   .......A.. .......A.. .T...L.R.. H.IE..VRNA .........A ...VT.LQ.. PALDK..K.-
5)   ...N...... D......L..G T.D..VN... ...T..N... R.........L ...C..L.CI PALDS-.TP- 430
1)   -HDDEKVGYE IIMRAIKAPL AQIAINAGYD GGVVVNEVEK HEGHFGFNAS NGKYVDMFKE GIIDPLKVER    498
2)   -NEEQN..IA LLR..VES.V R..VA...DE PS...DK.KQ GS.NY....A T.V.G..IEM ..L..A..T.
3)   TNE..QI.AR .VLK.LS... K...A...KE .AIIFQQ.MS RSANE.YD.L RDA.T..LEA ..L..A..T.
4)   T-G..AT.AN .VKV.LE... K...F.S.ME P...AEK.RN LSVGH.L..A T.E.E.LL.A .VA..V..T.
5)   ANE.Q.I.I. ..K.TL.I.A MT..K...VE .SLI.EKIMQ SSSEV.YD.M A.DF.N.VEK ....T..V.

499                                                    546
1)   IALQNAVSVS SLLLTTEATV HEIKEEKATP AMPDMGGMGG MGGMGGMM*
2)   S...A.A.IG G.MI....M. A..V.D.--. ..GG.PD... .......*
3)   S..ES.A.VA G........ LI A..P...PAA .-.A.P..-A. .DY*
4)   S....A.IA G.F.....V. ADKP.KT.A. .SDPT..... .DF*
5)   T...LD.AG.A ...T.A.VV. T..PK.EKD. G.GA..... GM.-...F*
```

FIG. 2(c)

```
              10                    30                    50
AAGCTTGCTGTCATGATCACAAAAAACACTAAAAAACATTATTATTAAGGATACAAAATG
                                                            M
              70                    90                   110
GCAAAAGAAATCAAATTTTCAGATAGTGCGAGAAACCTTTTATTTGAAGGCGTGAGGCAA
 A  K  E  I  K  F  S  D  S  A  R  N  L  L  F  E  G  V  R  Q
             130                   150                   170
CTCCATGACGCTGTCAAAGTAACCATGGGGCCAAGAGGCAGGAATGTATTGATCCAAAAA
 L  H  D  A  V  K  V  T  M  G  P  R  G  R  N  V  L  I  Q  K
             190                   210                   230
AGCTATGGCGCTCCAAGCATCACCAAAGACGGCGTGAGCGTGGCTAAAGAGATTGAATTA
 S  Y  G  A  P  S  I  T  K  D  G  V  S  V  A  K  E  I  E  L
             250                   270                   290
AGTTGCCCAGTAGCTAACATGGGCGCTCAACTCGTTAAAGAAGTAGCGAGCAAAACCGCT
 S  C  P  V  A  N  M  G  A  Q  L  V  K  E  V  A  S  K  T  A
             310                   330                   350
GATGCTGCCGGCGATGGCACGACCACAGCGACCGTGCTAGCTTATAGCATTTTTAAAGAA
 D  A  A  G  D  G  T  T  T  A  T  V  L  A  Y  S  I  F  K  E
             370                   390                   410
GGTTTGAGGAATATCACGGCTGGGGCTAACCCTATTGAAGTGAAACGAGGCATGGATAAA
 G  L  R  N  I  T  A  G  A  N  P  I  E  V  K  R  G  M  D  K
             430                   450                   470
GCTGCTGAAGCGATCATTAATGAGCTTAAAAAAGCGAGCAAAAAAGTAGGCGGTAAAGAA
 A  A  E  A  I  I  N  E  L  K  K  A  S  K  K  V  G  G  K  E
             490                   510                   530
GAAATCACCCAAGTGGCGACCATTTCTGCAAACTCCGATCACAATATCGGGAAACTCATC
 E  I  T  Q  V  A  T  I  S  A  N  S  D  H  N  I  G  K  L  I
             550                   570                   590
GCTGACGCTATGGAAAAAGTGGGTAAAGACGGCGTGATCACCGTTGAGGAAGCTAAGGGC
 A  D  A  M  E  K  V  G  K  D  G  V  I  T  V  E  E  A  K  G
             610                   630                   650
ATTGAAGATGAATTGGATGTCGTAGAAGGCATGCAATTTGATAGAGGCTACCTCTCCCCT
 I  E  D  E  L  D  V  V  E  G  M  Q  F  D  R  G  Y  L  S  P
```

FIG. 3(a)

```
       670                690                710
TATTTTGTAACGAACGCTGAGAAAATGACCGCTCAATTGGATAATGCTTACATCCTTTTA
 Y  F  V  T  N  A  E  K  M  T  A  Q  L  D  N  A  Y  I  L  L
       730                750                770
ACGGATAAAAAAATCTCTAGCATGAAGACATTCTCCCGCTACTAGAAAAAACCATGAAA
 T  D  K  K  I  S  S  M  K  D  I  L  P  L  L  E  K  T  M  K 790                810              HindIII
GAGGGCAAACCGCTTTTAATCATCGCTGAAGACATTGAGGGCGAAGCTTTAACGACTCTA
 E  G  K  P  L  L  I  I  A  E  D  I  E  G  E  A  L  T  T  L
       850                870                890
GTGGTGAATAAATTAAGAGGCGTGTTGAATATCGCAGCGGTTAAAGCTCCAGGCTTTGGG
 V  V  N  K  L  R  G  V  L  N  I  A  A  V  K  A  P  G  F  G
       910                930                950
GACAGAAGAAAAGAAATGCTCAAAGACATCGCTATTTTAACCGGCGGTCAAGTCATTAGC
 D  R  R  K  E  M  L  K  D  I  A  I  L  T  G  G  Q  V  I  S
       970                990               1010
GAAGAATTGGGCTTGAGTCTAGAAAACGCTGAAGTGGAGTTTTTAGGCAAAGCTGGAAGG
 E  E  L  G  L  S  L  E  N  A  E  V  E  F  L  G  K  A  G  R
       1030               1050               1070
ATTGTGATTGACAAAGACAACACCACGATCGTAGATGGCAAAGGCCATAGCGATGATGTT
 I  V  I  D  K  D  N  T  T  I  V  D  G  K  G  H  S  D  D  V
       1090               1110               1130
AAAGACAGAGTCGCGCAGATCAAAACCCAAATTGCAAGTACGACAAGCGATTATGACAAA
 K  D  R  V  A  Q  I  K  T  Q  I  A  S  T  T  S  D  Y  D  K
       1150               1170               1190
GAAAAATTGCAAGAAAGATTGGCTAAACTCTCTGGCGGTGTGGCTGTGATTAAAGTGGGC
 E  K  L  Q  E  R  L  A  K  L  S  G  G  V  A  V  I  K  V  G
       1210               1230               1250
GCTGCGAGTGAAGTGGAAATGAAAGAGAAAAAAGACCGGGTGGATGACGCGTTGAGCGCG
 A  A  S  E  V  E  M  K  E  K  K  D  R  V  D  D  A  L  S  A
       1270               1290               1310
ACTAAAGCGGCGGTTGAAGAAGGCATTGTGATTGGTGGCGGTGCGGCTCTCATTCGCGCG
 T  K  A  A  V  E  E  G  I  V  I  G  G  G  A  A  L  I  R  A
```

FIG. 3(b)

```
            1330              1350                1370
GCTCAAAAAGTGCATTTGAATTTGCACGATGATGAAAAAGTGGGCTATGAAATCATCATG
 A  Q  K  V  H  L  N  L  H  D  D  E  K  V  G  Y  E  I  I  M
            1390              1410                1430
CGCGCCATTAAAGCCCCATTAGCTCAAATCGCTATCAACGCTGGTTATGATGGCGGTGTG
 R  A  I  K  A  P  L  A  Q  I  A  I  N  A  G  Y  D  G  G  V
            1450              1470                1490
GTCGTGAATGAAGTAGAAAAACACGAAGGGCATTTTGGTTTTAACGCTAGCAATGGCAAG
 V  V  N  E  V  E  K  H  E  G  H  F  G  F  N  A  S  N  G  K
            1510              1530                1550
TATGTGGATATGTTTAAAGAAGGCATTATTGACCCCTTAAAAGTAGAAAGGATCGCTCTA
 Y  V  D  M  F  K  E  G  I  I  D  P  L  K  V  E  R  I  A  L
            1570              1590                1610
CAAAATGCGGTTTCGGTTTCAAGCCTGCTTTTAACCACAGAAGCCACCGTGCATGAAATC
 Q  N  A  V  S  V  S  S  L  L  L  T  T  E  A  T  V  H  E  I
            1630              1650                1670
AAAGAAGAAAAAGCGACTCCGGCAATGCCTGATATGGGTGGCATGGGCGGTATGGGAGGC
 K  E  E  K  A  T  P  A  M  P  D  M  G  G  M  G  G  M  G  G
            1690              1710                1730
ATGGGCGGCATGATGTAAGCCCGCTTGCTTTTAGTATAATCTGCTTTTAAAATCCCTTC
 M  G  G  M  M  *
            1750              1770                1790
TCTAAATCCCCCCCTTTCTAAAATCTCTTTTTTGGGGGGGTGCTTTGATAAAACCGCTCG 1810              1830
CTTGTAAAAACATGCAACAAAAAATCTCTGTTAAGCTT
```

FIG. 3(c)

CONJUGATES FORMED FROM HEAT SHOCK PROTEINS AND OLIGO-OR POLYSACCHARIDES

CROSS-REFERENCE TO RELATED APPLICATIONS

This application is the national phase of international application PCT/EP93/00516, filed Mar. 8, 1993. This application claims priority from application F192A000058, filed Mar. 6, 1992.

FIELD OF THE INVENTION

The present invention relates to conjugated compounds consisting of heat shock proteins and polysaccharides or oligosaccharides, in particular those polysaccharides or oligosaccharides derived from the capsule of pathogenic microorganisms. Such compounds are capable of inducing the formation of anti-polysaccharide antibodies and are accordingly useful as vaccines for use in man and in animals.

STATE OF THE ART

Bacteria are the aetiological agents for a wide range of disease conditions.

Examples of such diseases include meningitis caused by *Neisseria meningitidis* and other infections caused by *Haemophilus influenzae* Type b (Hib) or Streptococcus (including Pneumococcus), typhoid fever caused by infection with *Salmonella typhi*, intestinal disease caused by non-typoidal Salmonella or Shigella bacteria.

It is known that protective immunity to capsular bacteria is mediated by antibodies to the capsular polysaccharides. It is also known that, in order to obtain sufficient stimulation of the immune system, it is necessary to conjugate capsular polysaccharides to carrier proteins (Robbins et al, J. Infect. Dis., 1990, 161,821–832).

In particular, there have been described in the literature conjugated compounds consisting of polysaccharides (for example Group C meningococcal polysaccharide (MenC), Hib and Group A meningococcal polysaccharide (MenA)) and proteins such as CRM-197 (a peptide derived from *Corynebacterium diphtheriae*), TD (Diphtheria toxoid) or TT (Tetanus toxoid—see Peeters et al. Inf.Immun., (October 1991), 3504–3510; Claesson et al., J. Pediatrics St Louis, 112(5), 695–702, (May 1988).

Some such vaccines are already used with good results in clinical practice. However, there exists the need to identify novel protein carriers which impart to the conjugates immunogenic properties better than those achieved with the carriers used hitherto.

The present invention relates to the use of heat shock proteins as a protein carrier to increase the immunogenic response of oligosaccharides and polysaccharides.

Heat shock proteins are known to contain a significant number of T epitopes and thus to stimulate the cellular immune system.

A conjugated compound of the heat shock protein of *Mycobacterium bovis* (65 kDa), as a carrier for a malarial epitope, has been described as inducing a marked immunity in animals pre-immunised with Bacillus Calmette-Guérin (BCG) without requiring adjuvants (Lussow et al Eur. J. Immunol., 1991, 21,2297–2302). It is however to be noted that the effects observed in Lussow et al relate to T cell dependent effects exhibited by peptides (which are well known to be T-cell dependent) conjugated to heat shock proteins.

More particularly, because the heat shock proteins are well conserved across bacteria of different strains and type, adventitious infection with bacteria, which is a continuous process, will ensure that the immune system remains sensitised to heat shock proteins, thus ensuring a good response to the conjugate compounds of the invention either at primary vaccination or on administration of a booster vaccination.

The present invention permits the use of bacterial capsular polysaccharides and oligosaccharides to be used without adjuvants (although adjuvants can be used).

Large numbers of children are given BCG vaccine (which will include bacterial heat shock proteins) to guard against tuberculosis and therefore a conjugate of the present invention containing a heat shock protein as the carrier would find a large number of subjects already pre-immunised with the carrier precisely as a result of the BCG vaccination which they have undergone.

Again, since the heat shock proteins are highly conserved even the population which has not been vaccinated with BCG can easily develop immunity (as a result of natural interaction with other bacteria) and can hence find itself in a state of being able to develop a good immune response following vaccination with a conjugate composed of a heat shock protein and a T cell-independent antigen (oligosaccharide or polysaccharide). Thus the carriers of the present invention uniquely exploit the high conservation of heat shock proteins across bacteria and T-cell memory to ensure high titre vaccination.

SUMMARY OF THE INVENTION

According to the present invention, there is provided a conjugate compound comprising at least one heat shock protein or portion thereof including at least one immunostimulatory domain and at least one oligosaccharide or polysaccharide.

The heat shock protein may be any heat shock protein capable of exhibiting an immunostimulatory effect in animals, preferably humans.

The heat shock proteins are highly conserved in bacteria, parasites and mammals. Any heat shock protein can be used in the conjugates of the present invention, provided it exhibits a positive immunostimulatory effect in the intended immunisation subject without significant deleterious effects. Specific, non-limiting examples include heat shock proteins from *Helicobacter pylori, P. aeruginosa, C. trachomatis* and *M. leprae*, especially the hsp60 group of heat shock proteins.

More particularly, three heat shock proteins are specifically exemplified herein, namely, *M. bovis* BCG GroEL-type 65 kDa hsp (hspR65), Recombinant *M.tuberculosis* DnaK-type 70 kDa hsp (hspR70) and a novel heat shock protein from *H.pylori*.

The *H. pylori* heat shock protein (hsp) is a protein whose nucleotide and amino acid sequence is given in FIG. 3 and whose molecular weight is in the range of 54–62 kDa, preferably about 58–60 kDa. This hsp belongs to the group of Gram negative bacteria heat shock proteins, hsp60. In general, hsp are among the most conserved proteins in all living organisms, either prokaryotic and eukaroytic, animals and plants, and the conservation is spread along the whole sequence.

The conjugate may contain one or more heat shock proteins or immunostimulatory domains thereof. The heat shock proteins may the same or different. Preferably however, one heat shock protein or a portion containing one or more immunostimulatory domains is present.

As used herein, the term "immunostimulatory domain" refers to a region of a heat shock protein amino acid sequence capable of enhancing the immune reaction of a subject mammal to a polysaccharide or oligosaccharide component of a conjugate compound including the domain.

An advantage of using only specific domains from complete heat shock proteins is that it is possible selectively not to include domains common to human heat shock proteins. For human vaccination this is advantageous as such regions will not affect the immunostimulatory effect of the heat shock protein as they will be recognized as "self". In addition any immunity that is stimulated against such "self" regions might lead to autoimmunity.

Suitable domains of the hsp60 family of heat shock protein are identified in FIG. 2 by underlining of sequence of reduced homology with the human heat shock protein. Functional sub domains within the domains shown in FIG. 2 (SEQ. ID NO: 1); (SEQ. ID NO: 2); (SEQ. ID NO: 3); (SEQ. ID NO: 4); and (SEQ. ID NO: 5) may also be used, as can domain and sub domain combinations.

The skilled man can readily ascertain for a given heat shock protein which domains or epitopes are responsible for the immunostimulatory action and prepare modified heat shock protein containing only those domains or a sub set thereof.

The oligosaccharide or polysaccharide component of the conjugate compound may be the complete capsular polysaccharide or oligosaccharide of any pathogenic microorganism against which vaccination is indicated or a portion thereof capable of eliciting protective immunity. The oligosaccharide or polysaccharide may be from a single bacteria or from two or more bacteria.

Particular non-limiting examples of bacteria which may be targeted include: *Haemophilus influenzae* Type b (Hib), Streptococcus (including pneumococcus), Salmonella especially *Salmonella typhi*, intestinal disease caused by nontypoidal Salmonella or Shigella bacteria.

According to a particular embodiment of the invention, there have been prepared conjugates consisting of oligosaccharides of the Meningococci C (MenC) group and hsp.

According to a further particular embodiment of the present invention the hsp used for this purpose are hspR65 and hspR70.

In a second aspect of the invention, there is provided a process for producing conjugate compounds according to the present invention which comprises covalently bonding a heat shock protein or portion thereof including at least one immunostimulatory domain thereof to at least one oligosaccharide or polysaccharide.

The oligosaccharide or polysaccharide is preferably isolated from the bacterium to be targetted, but may be produced synthetically.

The heat shock protein may be isolated from its naturally occurring source or produced synthetically. Preferably the heat shock protein is produced by recombinant DNA technology using the techniques described in the general of the description herein.

Preferably the oligosacpharide or polysacoharide is modified prior to conjugation with the heat shock protein or portion thereof to provide reactive sites for conjugation. Suitably this involves introducing active functional groups, such as amino groups at the end groups of the oligosaccharide or polysaccharide. The thus modified oligosaccharide or polysaccharide may then be activated using a linking group, such as succinimide and conjugated to the heat shock protein or portion thereof.

In a third aspect of the invention, there is provided a conjugate compound according to the first aspect of the invention for use as a pharmaceutical, preferably as vaccine.

In a fourth aspect of the invention, there is provided the use of the conjugate compound according to the first aspect of the invention in the manufacture of a medicament for vaccination against bacterial infection.

In a fifth aspect of the invention, there is provided a method of vaccination comprising administering an immunologically effective amount of a conjugate compound according to the first aspect of the invention.

In a sixth aspect of the invention, there is provided a vaccine or therapeutic composition comprising one or more conjugate compounds according to the first aspect of the invention and a pharmaceutically acceptable carrier.

Preferably the composition is a vaccine composition and may include other excipients such as adjuvants, as necessary (see Section entitled "Vaccines" in the description below).

In a seventh aspect of the invention, there is provided a method for the preparation of a vaccine comprising bringing one or more conjugate compounds of the first aspect of the invention into association with a pharmaceutically acceptable carrier and optionally an adjuvant.

BRIEF DESCRIPTION OF THE DRAWINGS

In FIG. 1A the mice were preimmunized with BCG and in FIG. 1B they were not. The Figures show the results with hspR65-MenC (○) conjugate or hspR70-MenC (◇) conjugate, in PBS. Control groups of mice were immunised with the MenC oligosaccharide alone (Δ) or with a CRM197-MenC conjugate vaccine in aluminium hydroxide (□).

FIGS. 2a–c (SEQ. ID NO: 1); (SEQ. ID NO: 2); (SEQ. ID NO: 3); (SEQ. ID NO: 4); and (SEQ. ID NO: 5) show the amino acid sequence of the *Helicobacter pylori* heat shock protein and compares it with related heat shock proteins from *P. aeruginosa, C.trachomatis, M. leprae* and *H. sapiens*. The bars under the sequence indicate domains on reduced homology between sequences 1 to 4 and the human heat shock protein.

FIGS. 3a–c (SEQ. ID NO: 1); (SEQ. ID NO: 2); (SEQ. ID NO: 3); (SEQ. ID NO: 4); and (SEQ. ID NO: 5) are the nucleotide and amino acid sequences of the *Helicobacter pylori* heat shock protein.

DETAILED DESCRIPTION OF EMBODIMENTS

1. GENERAL METHODOLOGY

Figure 1A:
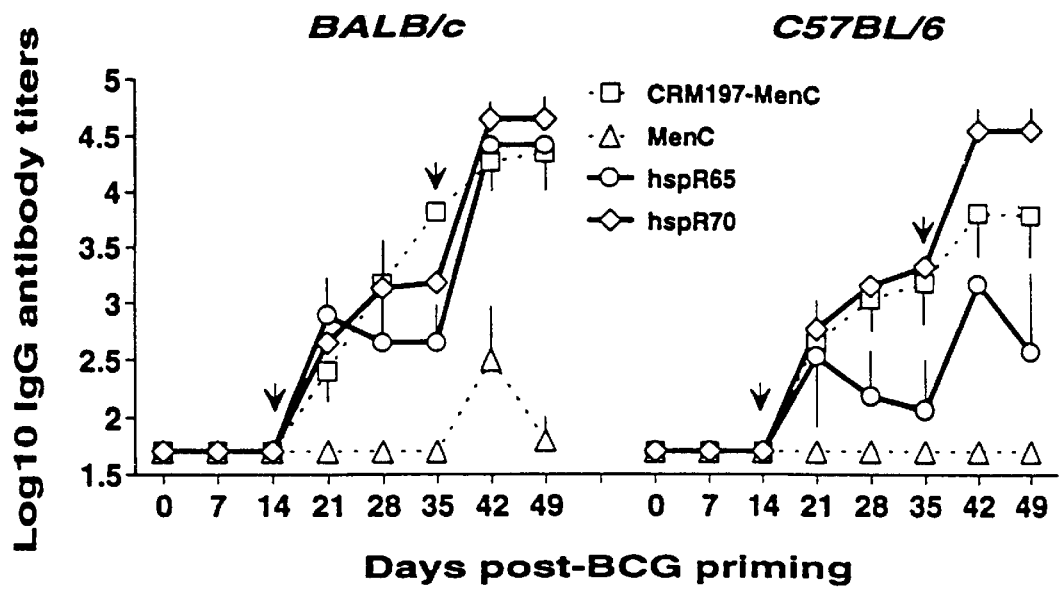
FIGS. 1A–B shows the results of immunising mice with a hspR65/MenC conjugate and comprises ELISA results for anti-MenC in the blood.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, et al., *MOLECULAR CLONING*; A LABORATORY MANUAL, SECOND EDITION (1989); *DNA CLONING*, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I–IV (D. M. Weir and C. C. Blackwell eds 1986).

Standard abbreviations for nucleotides and amino acids are used in this specification. All publications, patents, and patent applications cited herein are incorporated by reference.

2. DEFINITIONS

Heat shock proteins that can be used in the present invention include those polypeptides mentioned above and polypeptides with minor amino acid variations from the natural amino acid sequence of the protein; in particular, conservative amino acid replacements are contemplated.

Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonably predictable that an isolated replacement of a leucine with an isoleucine or valine, an aspartate with a glutamate, a threonine with a serine, or a similar conservative replacement of an amino acid with a structurally related amino acid will not have a major effect on the biological activity. Polypeptide molecules having substantially the same amino acid sequence as the protein but possessing minor amino acid substitutions that do not substantially affect the functional aspects are within the definition of the protein.

A significant advantage of producing the heat shock protein by recombinant DNA techniques rather than by isolating and purifying a protein from natural sources is that equivalent quantities of the protein can be produced by using less starting material than would be required for isolating the protein from a natural source. Producing the protein by recombinant techniques also permits the protein to be isolated in the absence of some molecules normally present in cells. Indeed, protein compositions entirely free of any trace of human protein contaminants can readily be produced because the only human protein produced by the recombinant non-human host is the recombinant protein at issue. Potential viral agents from natural sources and viral components pathogenic to humans are also avoided.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term "polynucleotide" as used herein refers to a polymeric form of a nucleotide of any length, preferably deoxyribonucleotides, and is used interchangeably herein with the terms "oligonucleotide" and "oligomer." The term refers only to the primary structure of the molecule. Thus, this term includes double- and single-stranded DNA, as well as antisense polynucleotides. It also includes known types of modifications, for example, the presence of labels which are known in the art, methylation, end "caps," substitution of one or more of the naturally occurring nucleotides with an analog, internucleotide modifications such as, for example, replacement with certain types of uncharged linkages (e.g., methyl phosphonates, phosphotriesters, phosphoamidates, carbamates, etc.) or charged linkages (e.g., phosphorothioates, phosphorodithioates, etc.), introduction of pendant moieties, such as, for example, proteins (including nucleases, toxins, antibodies, signal peptides, poly-L-lysine, etc.), intercalators (e.g., acridine, psoralen, etc.), chelators (e.g., metals, radioactive species, boron, oxidative moieties, etc.), alkylators (e.g., alpha anomeric nucleic acids, etc.).

By "genomic" is meant a collection or library of DNA molecules which are derived from restriction fragments that have been cloned in vectors. This may include all or part of the genetic material of an organism.

By "cDNA" is meant a complementary mRNA sequence that hybridizes to a complimentary strand of mRNA.

As used herein, the term "oligomer" refers to both primers and probes and is used interchangeably herein with the term "polynucleotide." The term oligomer does not connote the size of the molecule. However, typically oligomers are no greater than 1000 nucleotides, more typically are no greater than 500 nucleotides, even more typically are no greater than 250 nucleotides; they may be no greater than 100 nucleotides, and may be no greater than 75 nucleotides, and also may be no greater than 50 nucleotides in length.

The term "primer" as used herein refers to an oligomer which is capable of acting as a point of initiation of synthesis of a polynucleotide strand when used under appropriate conditions. The primer will be completely or substantially complementary to a region of the polynucleotide strand to be copied. Thus, under conditions conducive to hybridization, the primer will anneal to the complementary region of the analyte strand. Upon addition of suitable reactants, (e.g., a polymerase, nucleotide triphosphates, and the like), the primer will be extended by the polymerizing agent to form a copy of the analyte strand. The primer may be single-stranded or alternatively may be partially or fully double-stranded.

The terms "analyte polynucleotide" and "analyte strand" refer to a single- or double-stranded nucleic acid molecule which is suspected of containing a target sequence, and which may be present in a biological sample.

As used herein, the term "probe" refers to a structure comprised of a polynucleotide which forms a hybrid structure with a target sequence, due to complementarily of at least one sequence in the probe with a sequence in the target region. The polynucleotide regions of probes may be composed of DNA, and/or RNA, and/or synthetic nucleotide analogs. Included within probes are "capture probes" and "label probes".

As used herein, the term "target region" refers to a region of the nucleic acid which is to be amplified and/or detected. The term "target sequence" refers to a sequence with which a probe or primer will form a stable hybrid under desired conditions.

The term "capture probe" as used herein refers to a polynucleotide probe comprised of a single-stranded polynucleotide coupled to a binding partner. The single-stranded polynucleotide is comprised of a targeting polynucleotide sequence, which is complementary to a target sequence in a target region to be detected in the analyte polynucleotide. This complementary region is of sufficient length and complementarily to the target sequence to afford a duplex of stability which is sufficient to immobilize the analyte polynucleotide to a solid surface (via the binding partners). The binding partner is specific for a second binding partner; the second binding partner can be bound to the surface of a solid support, or may be linked indirectly via other structures or binding partners to a solid support.

The term "targeting polynucleotide sequence" as used herein refers to a polynucleotide sequence which is comprised of nucleotides which are complementary to a target nucleotide sequence; the sequence is of sufficient length and complementarily with the target sequence to form a duplex which has sufficient stability for the purpose intended.

The term "binding partner" as used herein refers to a molecule capable of binding a ligand molecule with high specificity, as for example an antigen and an antibody specific therefor. In general, the specific binding partners must bind with sufficient affinity to immobilize the analyte copy/complementary strand duplex (in the case of capture probes) under the isolation conditions. Specific binding partners are known in the art, and include, for example, biotin and avidin or streptavidin, IgG and protein A, the numerous known receptor-ligand couples, and complementary polynucleotide strands. In the case of complementary polynucleotide binding partners, the partners are normally at least about 15 bases in length, and may be at least 40 bases in length; in addition, they have a content of Gs and Cs of at least about 40% and as much as about 60%. The polynucleotides may be composed of DNA, RNA, or synthetic nucleotide analogs.

The term "coupled" as used herein refers to attachment by covalent bonds or by strong non-covalent interactions (e.g., hydrophobic interactions, hydrogen bonds, etc.). Covalent bonds may be, for example, ester, ether, phosphoester, amide, peptide, imide, carbon-sulfur bonds, carbon-phosphorus bonds, and the like.

The term "support" refers to any solid or semi-solid surface to which a desired binding partner may be anchored. Suitable supports include glass, plastic, metal, polymer gels, and the like, and may take the form of beads, wells, dipsticks, membranes, and the like.

The term "label" as used herein refers to any atom or moiety which can be used to provide a detectable (preferably quantifiable) signal, and which can be attached to a polynucleotide or polypeptide.

As used herein, the term "label probe" refers to a polynucleotide probe which is comprised of a targeting polynucleotide sequence which is complementary to a target sequence to be detected in the analyte polynucleotide. This complementary region is of sufficient length and complementarily to the target sequence to afford a duplex comprised of the "label probe" and the "target sequence" to be detected by the label. The label probe is coupled to a label either directly, or indirectly via a set of ligand molecules with high specificity for each other, including multimers.

The term "multimer," as used herein, refers to linear or branched polymers of the same repeating single-stranded polynucleotide unit or different single-stranded polynucleotide units. At least one of the units has a sequence, length, and composition that permits it to hybridize specifically to a first single-stranded nucleotide sequence of interest, typically an analyte or a polynucleotide probe (e.g., a label probe) bound to an analyte. In order to achieve such specificity and stability, this unit will normally be at least about 15 nucleotides in length, typically no more than about 50 nucleotides in length, and preferably about 30 nucleotides in length; moreover, the content of Gs and Cs will normally be at least about 40%, and at most about 60%. In addition to such unit(s), the multimer includes a multiplicity of units that are capable of hybridizing specifically and stably to a second single-stranded nucleotide of interest, typically a labelled polynucleotide or another multimer. These units are generally about the same size and composition as the multimers discussed above. When a multimer is designed to be hybridized to another multimer, the first and second oligonucleotide units are heterogeneous (different), and do not hybridize with each other under the conditions of the selected assay. Thus, multimers may be label probes, or may be ligands which couple the label to the probe.

A "replicon" is any genetic element, e.g., a plasmid, a chromosome, a virus, a cosmid, etc. that behaves as an autonomous unit of polynucleotide replication within a cell; i.e., capable of replication under its own control. This may include selectable markers.

"PCR" refers to the technique of polymerase chain reaction as described in Saiki, et al., Nature 324:163 (1986); and Scharf et al., Science (1986) 233:1076–1078; and U.S. Pat. No. 4,683,195; and U.S. Pat. No. 4,683,202.

As used herein, x is "heterologous" with respect to y if x is not naturally associated with y in the identical manner; i.e., x is not associated with y in nature or x is not associated with y in the same manner as is found in nature.

"Homology" refers to the degree of similarity between x and y. The correspondence between the sequence from one form to another can be determined by techniques known in the art. For example, they can be determined by a direct comparison of the sequence information of the polynucleotide. Alternatively, homology can be determined by hybridization of the polynucleotides under conditions which form stable duplexes between homologous regions (for example, those which would be used prior to $S_1$ digestion), followed by digestion with single-stranded specific nuclease(s), followed by size determination of the digested fragments.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression, and may also include additional components whose presence is advantageous, for example, leader sequences and fusion partner sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, cDNA, and recombinant polynucleotide sequences.

As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

"Immunogenic" refers to the ability of a polypeptide to cause a humonal and/or cellular immune response, whether alone or when linked to a carrier, in the presence or absence of an adjuvant. "Neutralization" refers to an immune response that blocks the infectivity, either partially or fully, of an infectious agent. "Epitope" refers to an antigenic determinant of a peptide, polypeptide, or protein; an epitope can comprise 3 or more amino acids in a spatial conformation unique to the epitope. Generally, an epitope consists of at least 5 such amino acids and, more usually, consists of at least 8–10 such amino acids. Methods of determining spatial conformation of amino acids are known in the art and include, for example, x-ray crystallography and 2-dimensional nuclear magnetic resonance. Antibodies that recognize the same epitope can be identified in a simple immunoassay showing the ability of one antibody to block the binding of another antibody to a target antigen.

"Treatment," as used herein, refers to prophylaxis and/or therapy (i.e., the modulation of any disease symptoms). An "individual" indicates an animal that is susceptible to infection by bacterium possessing an antigenic capsular polysaccharide or oligosaccharide structure and includes, but is not limited to, primates, including humans. A "vaccine" is an immunogenic, or otherwise capable of eliciting protection against such a bacterium, whether partial or complete, composition useful for treatment of an individual.

The conjugate compounds of the invention may be used for producing antibodies, either monoclonal or polyclonal, specific to the proteins. The methods for producing these antibodies are known in the art.

"Recombinant host cells", "host cells," "cells," "cell cultures," and other such terms denote, for example, microorganisms, insect cells, and mammalian cells, that can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. Examples for mammalian host cells include Chinese hamster ovary (CHO) and monkey kidney (COS) cells.

Specifically, as used herein, "cell line," refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. The term "cell lines" also includes immortalized cells. Preferably, cell lines include nonhybrid cell lines or hybridomas to only two cell types.

As used herein, the term "microorganism" includes prokaryotic and eukaryotic microbial species such as bacteria and fungi, the latter including yeast and filamentous fungi.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

By "purified" and "isolated" is meant, when referring to a polypeptide or nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present (but water, buffers, and other small molecules, especially molecules having a molecular weight of less than 1000, can be present).

3. EXPRESSION SYSTEMS

Once the appropriate heat shock protein coding sequence is isolated, it can be expressed in a variety of different expression systems; for example those used with mammalian cells, baculoviruses, bacteria, and yeast.

3.1. Mammalian Systems

Mammalian expression systems are known in the art. A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25–30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation, Sambrook et al., *Molecular Cloning: A Laboratory Manual*, 2nd ed (1989).

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter, Maniatis et al., Science 236:1237 (1989); Alberts et al. *Molecular Biology of the Cell*, 2nd ed (1989). Enhancer elements derived from viruses may be particularly useful, because they usually have a broader host range. Examples include the SV40 early gene enhancer, Dijkema et al (1985) EMBO J. 4:761, and the enhancer/promoters derived from the long terminal repeat (LTR) of the Rous Sarcoma Virus, Gorman et al. (1982) Proc. Natl. Acad. Sci. 79:6777, and from human cytomegalovirus, Boshart et al. (1985) Cell 41:5221. Additionally, some enhancers are regulatable and become active only in the presence of an inducer, such as a hormone or metal ion, Sassone-Corsi et al. (1986) Trends Genet. 2:215; Maniatis et al. (1987) Science 236:1237.

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus tripartite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation, Birnstiel et al. (1985) Cell 41:349; Proudfoot and Whitelaw (1988) "Termination and 3' end processing of eukaryotic RNA. In *Transcription and splicing* (ed. B. D. Hames and D. M. Glover); Proudfoot (1989) Trends Biochem. Sci. 14:105. These sequences direct the transcription of an mRNA which can be translated into the polypeptide encoded by the DNA. Examples of transcription terminator/polyadenylation signals include those derived from SV40, Sambrook et al (1989), *Molecular Cloning: A Laboratory Manual*.

Some genes may be expressed more efficiently when introns (also called intervening sequences) are present. Several cDNAs, however, have been efficiently expressed from vectors that lack splicing signals (also called splice donor and acceptor sites), see e.g., Gething and Sambrook (1981) Nature 293:620. Introns are intervening noncoding sequences within a coding sequence that contain splice donor and acceptor sites. They are removed by a process called "splicing," following polyadenylation of the primary transcript, Nevins (1983) Annu. Rev. Biochem. 52:441; Green (1986) Annu. Rev. Genet. 20:671; Padgett et al. (1986) Annu. Rev. Biochem. 55:1119; Krainer and Maniatis (1988) "RNA splicing," In Transcription and splicing (ed. B. D. Hames and D. M. Glover).

Usually, the above-described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require transacting factors to replicate. For example, plasmids containing the replication systems of papovaviruses, such as SV40, Gluzman (1981) Cell 23:175, or polyomavirus, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a procaryotic host for cloning and amplification. Examples of such mammalian-bacteria shuttle vectors include pMT2, Kaufman et al. (1989) Mol. Cell. Biol. 9:946, and PHEBO, Shimizu et al. (1986) Mol. Cell. Biol. 6:1074.

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art.

Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged, recombinant virus is expressed and recombinant plaques are identified and purified. Materials and methods for baculovirus/insect cell expression systems are commercially available in kit form from, inter alia, Invitrogen, San Diego, Calif. ("MAXBAC™" kit (expression system)). These techniques are generally known to those skilled in the art and fully described in Summers and Smith, Texas Agricultural Experiment Station Bulletin No. 1555 (1987) (hereinafter "Summers and Smith").

Prior to inserting the DNA sequence encoding the protein into the baculovirus genome, the above-described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, Virology (1989) 17:31.

The plasmid usually also contains the polyhedron polyadenylation signal (Miller et al. (1988) Ann. Rev. Microbiol., 42:177) and a procaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), J. Gen. Virol. 69:765.

DNA encoding suitable signal sequences can be derived from genes for secreted insect or baculovirus proteins, such as the baculovirus polyhedrin gene (Carbonell et al. (1988) Gene, 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), Nature 315:592; human gastrin-releasing peptide, Lebacq-Verheyden et al., (1988), Molec. Cell. Biol. 8:3129; human IL-2, Smith et al., (1985) Proc. Nat'l Acad. Sci. USA, 82:8404; mouse IL-3, (Miyajima et al., (1987) Gene 58:273; and human glucocerebrosidase, Martin et al. (1988) DNA 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2–5 kb section of the baculovirus genome. Methods for introducing heterologous DNA into the desired site in the baculovirus virus are known in the art. (See Summers and Smith; Ju et al. (1987); Smith et al., Mol. Cell. Biol. (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), Bioessays 4:91.

The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 μm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda,* and *Trichoplusia ni* (PCT Pub. No. Wo 89/046699; Carbonell et al., (1985) J. Virol. 56:153; Wright (1986) Nature 321:718; Smith et al., (1983) Mol. Cell. Biol. 3:2156; and see generally, Fraser, et al. (1989) In Vitro Cell. Dev. Biol. 25:225).

Cells and cell culture media are commercially available for both direct and fusion expression of heterologous polypeptides in a baculovirus/expression system; cell culture technology is generally known to those skilled in the art. See, e.g., Summers and Smith.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g., HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g., proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Bacterial Systems

Bacterial expression techniques are known in the art. A bacterial promoter is any DNA sequence capable of binding bacterial RNA polymerase and initiating the downstream (3") transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli*, Raibaud et al. (1984) Annu. Rev. Genet. 18:173. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac), Chang et al. (1977) Nature 198:1056, and maltose. Additional examples include promoter sequences derived from biosynthetic enzymes such as tryptophan (trp), Goeddel et al. (1980) Nuc. Acids Res. 8:4057; Yelverton et al. (1981) Nucl. Acids Res. 9:731; U.S. Pat. No. 4,738,921; EPO Publ. Nos. 036 776 and 121 775. The g-laotamase (bla) promoter system, Weissmann (1981) "The cloning of interferon and other mistakes." In Interferon 3 (ed. I. Gresser), bacteriophage lambda PL, Shimatake et al. (1981) Nature 292:128, and T5, U.S. Pat. No. 4,689,406, promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter, U.S. Pat. No. 4,551, 433. For example, the tac promoter is a hybrid trp-lac promoter comprised of both trp promoter and lac operon sequences that is regulated by the lac repressor, Amann et al. (1983) Gene 25:167; de Boer et al. (1983) Proc. Natl. Acad. Sci. 80:21. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system, Studier et al. (1986) J. Mol. Biol. 189:113; Tabor et al. (1985) Proc Natl. Acad. Sci. 82:1074. In addition, a hybrid promoter can also be comprised of a bacteriophage promoter and an *E. coli* operator region (EPO Publ. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon, Shine et al. (1975) Nature 254:34. The SD sequence is thought to promote binding of mRNA to the ribosome by the pairing of bases between the SD sequence and the 3' and of *E. coli* 16S rRNA, Steitz et al. (1979) "Genetic signals and nucleotide sequences in messenger RNA." In *Biological Regulation and Development: Gene Expression* (ed. R. F. Goldberger). To express eukaryotic genes and prokaryotic genes with weak ribosome-binding site, Sambrook et al. (1989), *Molecular Cloning: A Laboratory Manual.*

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO Publ. No. 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene, Nagai et al. (1984) Nature 309:810. Fusion proteins can also be made with sequences from the lacZ, Jia et al. (1987) Gene 60:197, trpE, Allen et al. (1987) J. Biotechnol. 5:93; Makoff et al. (1989) J. Gen. Microbiol. 135:11, and EPO Publ. No. 324 647, genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated. Miller et al. (1989) Bio/Technology 7:698.

Alternatively, foreign proteins can also be secreted from the cell by creating chimeric DNA molecules that encode a fusion protein comprised of a signal peptide sequence fragment that provides for secretion of the foreign protein in bacteria, U.S. Pat. No. 4,336,336. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA). Masui et al. (1983), in: *Experimental Manipulation of Gene Expression*; Ghrayeb et al. (1984) EMBO J. 3:2437 and the *E. coli* alkaline phosphatase signal sequence (phoA), Oka et al. (1985) Proc. Natl. Acad. Sci. 82:7212. As an additional example, the signal sequence of the alpha-amylase gene from various Bacillus strains can be used to secrete heterologous proteins from *B. subtilis*. Palva et al. (1982) Proc. Natl. Acad. Sci. USA 79:5582; EPO Publ. No. 244 042.

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above-described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The replicon will have a replication system, thus allowing it to be maintained in a procaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome (EPO Publ. No. 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline. Davies et al. (1978) Annu. Rev.Microbiol. 32:469. Selectable markers may also include biosynthetic genes, such as those in the histidine, tryptophan, and leucine biosynthetic pathways.

Alternatively, some of the above-described components can be put together in transformation vectors. Transformation vectors are usually comprised of a selectable marker that is either maintained in a replicon or developed into an integrating vector.

Expression and transformation vectors, either extrachromosomal replicons or integrating vectors, have been developed for transformation into many bacteria. For example, expression vectors have been developed for, inter alia, the following bacteria: *Bacillus subtilis*, Palv et al. (1982) Proc. Natl. Acad. Sci. USA 79:5582; EPO Publ. Nos. 036 259 and 063 953; PCT Publ. No. WO 84/04541; *E. coli*, Shimatake et al. (1981) Nature 292:128; Amann et al. (1985) Gene 40:183; Studier et al. (1986) J. Mol. Biol. 189:113; EPO Publ. Nos. 036 776, 136 829 and 136 907; *Streptococcus cremoris*, Powell et al. (1988) Appl. Environ. Microbiol. 54:655; *Streptococcus lividans*, Powell et al. (1988) Appl. Environ. Microbiol. 54:655; and *Streptomyces lividans*, U.S. Pat. No. 4,745,056.

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See, e.g., Masson et al. (1989) FEMS Microbiol. Lett. 60:273; Palva et al. (1982) Proc. Natl. Acad. Sci. USA 79:5582; EPO Publ. Nos. 036 259 and 063 953; PCT Publ. No. WO 84/04541, for Bacillus; Miller et al. (1988) Proc. Natl. Acad. Sci. 85:856; Wang et al. (1990) J. Bacteriol. 172:949, for Campylobacter; Cohen et al. (1973)

Proc. Natl. Acad. Sci. 69:2110; Dower et al. (1988) Nucleic Acids Res. 16:6127; Kushner (1978) "An improved method for transformation of *E. coli* with ColE1-derived plasmids," In *Genetic Engineering: Proceedings of the International Symposium on Genetic Engineering* (eds. H. W. Boyer and S. Nicosia); Mandel et al. (1970) J. Mol. Biol. 53:159; Taketo (1988) Biochim. Biophys. Acta 949:318, for Escherichia; Chassy et al. (1987) FEMS Microbiol. Lett. 44:173, for Lactobacillus; Fiedler et al. (1988) Anal. Biochem 170:38, for Pseudomonas; Augustin et al. (1990) FEMS Microbiol. Lett. 66:203, for Staphylococcus; Barany et al. (1980) J. Bacteriol. 144:698; Harlander (1987) "Transformation of *Streptococcus lactis* by electroporation, in: Streptococcal Genetics (ed. J. Ferretti and R. Curtiss III); Perry et al. (1981) Infec. Immun. 32:1295; Powell et al. (1988) Appl. Environ. Microbiol. 54:655; Somkuti et al. (1987) Proc. 4th Evr. Cong. Biotechnology 1:412, for Streptococcus.

iv. Yeast Expression

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EPO Publ. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO Publ. No. 329 203). The yeast PHO5 gene, encoding acid phosphatase, also provides useful promoter sequences, Myanohara et al. (1983) Proc. Natl. Acad. Sci. USA 80:1.

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. No. 4,876,197 and U.S. Pat. No. 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (EPO Publ. No. 164 556). Furthermore, a yeast promoter can include naturally occurring promoters of non-yeast origin that have the ability to bind yeast RNA polymerase and initiate transcription. Examples of such promoters include, inter alia, Cohen et al. (1980) Proc. Natl. Acad. Sci. USA 77:1078; Henikoff et al. (1981) Nature 283:835; Hollenberg et al. (1981) Curr. Topics Microbiol. Immunol. 96:119; Hollenberg et al. (1979) "The Expression of Bacterial Antibiotic Resistance Genes in the Yeast *Saccharomyces cerevisiae*," in: *Plasmids of Medical, Environmental and Commercial Importance* (eds. K. N. Timmis and A. Puhler); Mercerau-Puigalon et al. (1980) Gene 11:163; Panthier et al. (1980) Curr. Genet. 2:109.

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g., EPO Publ. No. 196 056. Another example is a ubiquitin fusion protein. Such a fusion protein is made with the ubiquitin region that preferably retains a site for a processing enzyme (e.g. ubiquitin-specific processing protease) to cleave the ubiquitin from the foreign protein. Through this method, therefore, native foreign protein can be isolated (see, e.g., PCT Publ. No. WO 88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EPO Publ. No. 012 873; JPO Publ. No. 62,096,086) and the A-factor gene (U.S. Pat. No. 4,588,684). Alternatively, leaders of non-yeast origin, such as an interferon leader, exist that also provide for secretion in yeast (EPO Publ. No. 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. No. 4,546,083 and U.S. Pat. No. 4,870,008; EPO Publ. No. 324 274). Additional leaders employing an alpha-factor leader fragment that provides for secretion include hybrid alpha-factor leaders made with a presequence of a first yeast, but a pro-region from a second yeast alphafactor. (See e.g., PCT Publ. No. WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above-described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24, Botstein et al. (1979) Gene 8:17–24; pCl/1, Brake et al. (1984) Proc. Natl. Acad. Sci USA 81:4642–4646; and YRp17, Stinchcomb et al. (1982) J. Mol. Biol. 158:157. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. A high or low copy number vector may be selected, depending upon the effect of the vector and the foreign protein on the host.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome, Orr-Weaver et al. (1983) Methods in Enzymol. 101:228–245. An integrating vector may be directed to a specific locus in yeast by selecting the appropriate homologous sequence for inclusion in the vector. One or more expression construct may integrate, possibly affecting levels of recombinant protein produced, Rine et al. (1983) Proc. Natl. Acad. Sci. USA 80:6750. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions. Butt et al. (1987) Microbiol, Rev. 51:351.

Alternatively, some of the above-described components can be put together into transformation vectors. Transformation vectors are usually comprised of a selectable marker that is either maintained in a replicon or developed into an integrating vector.

Expression and transformation vectors, either extrachromosomal replicons or integrating vectors, have been developed for transformation into many yeasts. For example, expression vectors have been developed for, inter alia, the following yeasts: *Candida albicans*, Kurtz, et al. (1986) Mol. Cell. Biol. 6:142; *Candida maltosa*, Kunze, et al. (1985) J. Basic Microbiol. 25:141; *Hansenula polymorpha*, Gleeson, et al. (1986) J. Gen. Microbiol. 132:3459; Roggenkamp et al. (1986) Mol. Gen. Genet. 202:302; *Kluyveromyces fragilis*, Das, et al. (1984) J. Bacteriol. 158:1165; *Kluyveromyces lactis*, De Louvencourt et al. (1983) J. Bacteriol. 154:737; Van den Berg et al. (1990) Bio/Technology 8:135; *Pichia quillerimondii*, Kunze et al. (1985) J. Basic Microbiol. 25:141; *Pichia pastoris*, Cregg, et al. (1985) Mol. Cell. Biol. 5:3376; U.S. Pat. No. 4,837,148 and U.S. Pat. No. 4,929,555; *Saccharomyces cerevisiae*, Hinnen et al. (1978) Proc. Natl. Acad. Sci. USA 75:1929; Ito et al. (1983) J. Bacteriol. 153:163; *Schizosaccharomyces pombe*, Beach et al. (1981) Nature 300:706; and *Yarrowia lipolytica*, Davidow, et al. (1985) Curr. Genet. 10:380471 Gaillardin, et al. (1985) Curr. Genet. 10:49.

Methods of introducing exogenous DNA into yeast hosts are well-known in the art, and usually include either the transformation of spheroplasts or of intact yeast cells treated with alkali cations. Transformation procedures usually vary with the yeast species to be transformed. See e.g., Kurtz et al. (1986) Mol. Cell. Biol. 6:142; Kunze et al. (1985) J. Basic Microbiol. 25:141, for Candida; Gleeson et al. (1986) J. Gen. Microbioy. 132:3459; Roggenkamp et al. (1986) Mol. Gen. Genet. 202:302, for Hansenula; Das et al. (1984) J. Bacteriol. 158:1165; De Louvencourt et al. (1983) J. Bacteriol. 154:1165; Van den Berg et al. (1990) Bio/Technology 8:135, for Kluvveromyces; Cregg et al. (1985) Mol. Cell. Biol. 5:3376; Kunze et al. (1985) J. Basic Microbiol. 25:141; U.S. Pat. No. 4,837,148 and U.S. Pat. No. 4,929,555, for Pichia; Hinnen et al. (1978) Proc. Natl. Acad. Sci. USA 75;1929; Ito et al. (1983) J. Bacteriol. 153:163, for Saccharomyces; Beach et al. (1981) Nature 300:706, for Schizosaccharomyces; Davidow et al. (1985) Curr. Genet. 10:39; Gaillardin et al. (1985) Curr. Genet. 10:49, for Yarrowia.

4. VACCINES

Each of the conjugate compounds discussed herein may be used as a sole vaccine candidate or in combination with one or more other antigens from other pathogenic sources. These vaccines may either be prophylactic (to prevent infection) or therapeutic (to treat disease after infection).

Such vaccines comprise the conjugate compound usually in combination with "pharmaceutically acceptable carriers", which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen may be conjugated to a bacterial toxoid, such as a toxoid from diphtheria, tetanus etc.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) RIBI™ (adjuvant system) (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS DETOX™ (monophosphorlipid A+cell wall skeleton); (3) saponin adjuvants, such as STIMULON™ (saponin adjuvant) (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc; and (6) other substances that act as immunostimulating agents to enhance the effectiveness of the composition. Alum and MF59 are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-huydroxyphosphoryloxy)-ethylamine (MTP-PE), etc.

The immunogenic compositions (e.g., the antigen, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

5. EXAMPLE 1

Conjugate compounds comprising polysaccharides of the Meningococci C group and heat shock proteins hspR70 and hspR65 were constructed and tested for vaccine efficacy

5.1. Purification of Polysaccharides of the Meningococci C (MenC) Group, and Production of MenC Oligosaccharides The meningococcal polysaccharide of group C was purified as described in Frasc C. E. "Advances in Biotechnological Processes: Bacterial vaccines" (A. Mizrahi, ed.), vol. 13, pp. 123–145, Wiley-Liss Inc., New York (1990). The purified polysaccharide (10 mg/ml) was depolymerised by hydrolysis in 0.01 M acetate buffer of pH 5, at 100° C. for 8 hours. The resulting product was analysed by analytical chromatography (on Sephadex 6–50) and exhibited a Kd (distribution coefficient) of 0.27.

5.2. Introduction of a Primary Amine Group into the Terminal Groups of the Oligosaccharide 0.5 M of ammonium chloride and 0.15 M of sodium cyanoborohydride were added to the solution obtained from the hydrolysis. The pH was raised to 7 and the resulting solution was kept at 35° C. for one week. The oligosaccharide was then purified by chromatography on Sephadex 6–15), the void volume fractions containing chemical activity in respect of the amine groups and carbohydrate groups being collected while those containing monomeric sugars and excess of reagents were discarded. The resulting MenC oligosaccharide was characterised by determining the amine groups, the sialic acid groups and the O-acetyl group. The following molar ratios were obtained: sialic acid/amine groups=20, O-acetyl/sialic acid=0.84.

5.3. Preparation of Heat Shock Proteins

*M. bovis* BCG GroEL-type 65 kDa hsp (hspR65) was expressed from a recombinant *E.coli* K12 strain harbouring plasmid pRIB1300 (Thole et al, Infect. Immun. 1985, 50, 800:Van Eden et al, Nature, 1988, 331,171) and purified as described in Thole et al, Infect. Immun., 1987, 55,1466.

Recombinant *M.tuberculosis* DnaK-type 70 kDa hsp (hspR70) was obtained and purified by ATP-agarose chromatography (Mehlert et al Mol. Microbiol., 1989, 3,125).

5.4. Preparation of the Glycoconjugates of MenC Polysaccharide and hspR65 and hspR70

The MenC amino-oligosaccharide was dissolved in dimethylsulphoxide with 10% of $H_2O$ and then caused to react with a 12-fold excess (relative to the amine groups) of the N-hydroxysuccinimide ester of adipic acid [prepared according to Hill et al. "FEBS LETT." 102:282 (1979)]. After purification by precipitation with dioxane (1–4-fold amount) the activated oligosaccharide was dried in vacuo and analysed for its content of N-hydroxysuccinimino ester. HspR65 and hspR70 in an amount of 5 mg/ml of 0.1 M phosphate buffer of pH 7 were then caused to react with a 300-fold molar excess of activated oligosaccharide. The glycoconjugates respectively obtained were freed from the unreacted oligosaccharides by chromatography, filtered and stored at 4° C. The ratio of their content of sialic acid to the percentage of sialic acid in the MenC polysaccharide starting material represents the amount of oligosaccharide which has been coupled. The protein content of the preparation was confirmed by the method of Lowry "J. Biol. Chem." 193:265 (1951). In particular, the conjugate with hspR70 has a protein content of 310 μg/ml and a saccharide content of 76 μg/ml whilst the conjugate with hspR65 has a protein content of 180 μg/ml and a saccharide content of 97 μg/ml.

5.5. Mice and Immunisation BALB/c ($H-2^d$), C567BL/6 ($H-2^b$) and CBA/J ($H-2^k$) female mice, 8–12 weeks old, were bred from in our breeding facilities.

The starting couples were provided by Jackson Laboratory, Bar Harbor, ME. BALB/c nu/nu athymic mice were obtained from Iffa Credo, L'Arbresle, France.

On day 0, each mouse received intraperitoneally $10^6$ CFU of BCG (or PBS in the case of the control group), followed by 2 doses of conjugate on days 14 and 35 (in PBS).

Control groups received the MenC oligosaccharide alone, or the MenC oligosaccharide—CRM197 conjugate vaccine adsorbed on aluminium hydroxide (1 mg/dose, in 0.5 ml). In each immunisation, the mice received 2 μg of MenC oligosaccharide, which corresponded to 8.7 μg of MenC oligosaccharide—CRM197 conjugate vaccine, 8.4 μg of the MenC oligosaccharide—hspR70 conjugate or 3.7 μg of the MenC oligosaccharide—hspR65 conjugate.

5.6. Determination of the Antibodies According to the ELISA Method

Each week, blood was taken from the retro-orbital plexus of the mouse and the antibodies were titrated with ELISA.

For determination of IgG anti-MenC antibodies, flat-based plates with 96 wells were covered with MenC polysaccharide (5 μg/ml) (Nunc Immunoplate I, Nunc, Roskilde, Denmark) in PBS, pH 7.4, by overnight incubation at 37° C. After repeated washings with PBS containing 0.05% of Tween-20 (PBS-T) and incubation for one hour at 37° C. with 200 μl of PBS-T containing 5% of FCS, the wells were incubated overnight at 4° C. with 100 μl of mouse serum diluted in PBS-T containing 5% of FCS. After repeated washings, the plates were again incubated for 3 hours at 37° C. with 100 μl of an appropriate dilution of an IgG anti-mouse anti-serum conjugated to peroxidase.

The presence of specific antibodies was revealed by addition of 2,2'-azino-bis-(3-ethylbenzothiazoline-sulphonic acid) (ABTS; Kirkegaard and Pery Laboratories Inc., Gaithersburg, Md.) as the substrate. The results were measured in terms of the absorbance at 414 nm. Samples of serum with an absorbance of less than 0.2 at the first dilution tested (1:50) were considered negative.

5.7. Carrier Effect of hpsR65 and hpsR70 Conjugated to Oligosaccharide

HspR65 and hspR70-MenC oligosaccharide conjugates were used to immunise BALB/c and C57BL/6 mice which had previously been sensitised with BCG or were non-sensitised.

As a control, groups of mice received MenC only or CRM 197-MenC conjugate vaccine in aluminium hydroxide.

Figure 1B:
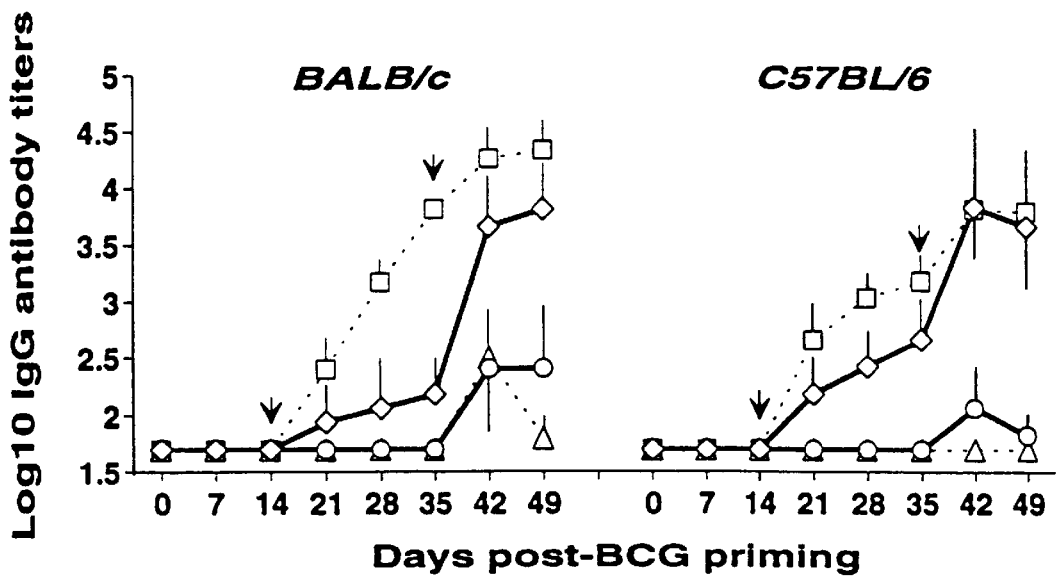

FIG. 1 shows that anti-MenC polysaccharide IgG antibodies were produced after immunisation with hsp-MenC conjugates in amounts comparable to, or greater than (C57BL/6 in FIG. 1A), those measured in the case of a CRM 197-MenC conjugate vaccine in aluminium hydroxide. This effect was observed not only in the case of the absence of adjuvant but also, in the case of the hspR70-MenC conjugate, in the absence of sensitisation with BCG (FIG. 1B). These results make it possible to state that immunisation using mycobacterial hsp in the absence of adjuvants and of sensitisation with BCG can indeed be achieved also with oligosaccharide antigens.

Accordingly it has been confirmed that the molecules of hsp, in particular hspR70, exert a powerful carrier effect also in mice not sensitised with BCG, and that hsp acts as a potent carrier of molecules capable of inducing IgG antibodies which are specific against the polysaccharide transported, even in the absence of the adjuvants.

This potent carrier effect of the mycobacterial hsp, exerted in the absence of adjuvants and of pre-sensitisation, makes the conjugates described particularly useful for the development of novel vaccines against bacterial infections.

6. EXAMPLE 2

A novel *H.pylori* heat shock protein was identified and produced using recombinant DNA techniques.

6.1. Materials and Methods

6.1.1. *H. pylori* strains and growth conditions

*H. pylori* strains used were: CCUG 17874, G39 and G33 (isolated from gastric biopsies in the hospital of Grosseto, Italy), Pylo 2U+ and Pylo 2U− (provided by F. Megraud, hospital Pellegzin, Bordeaux, France), BA96 (isolated by gastric biopsies at the University of Siena, Italy). Strain Pylo 2U+is noncytotoxic; strain Pylo 2U− is noncytotoxic and urease-negative. All strains were routinely grown on Columbia agar containing 0.2% of cyclodextrin, 5 μg/ml of cefsulodin and 5 μg/ml of amphotericin B under microaerophilic conditions for 5–6 days at 37° C. Cells were harvested and washed with PBS. The pellets were resuspended in Laemmli sample buffer and lysed by boiling.

Sera of patients affected by gastritis and ulcers (provided by A. Ponzetto, hospital "Le Molinette", Torino, Italy) and sera of patients with gastric carcinoma (provided by F. Roviello, University of Siena, Italy) were used.

6.1.2. Immunoscreening of the Library

Five hundred thousand plaques of a λgt11 *H. pylori* DNA expression library were mixed with 5 ml of a suspension of *E. coli* strain Y1090 grown O/N in LB with 0.2% Maltose and 10 mM $MgSO_4$, and resuspended in 10 mM $MgSO_4$ at 0.5 O.D. After 10 minutes incubation at 37° C., 75 ml of melted TopAgarose were poured in the bacterial/phage mix and the whole was plated on BBL plates (50,000 plaques/plate). After 3.5 hrs incubation of the plated library at 42° C., nitrocellulose filters (Schleicher and Schuell, Dassel, Germany), previously wet with 10 mM IPTG, were set on plates and incubation was prolonged for 3.5 hrs at 37° C. and then O/N at 4° C. Lifted filters with lambda proteins were rinse in PBS, and saturated in 5% nonfat dried milk dissolved in TBST (10 mM TRIS pH 8, 100 mM NaCl, 5M $MgCl_2$) for 20'. The first hybridization step was performed with the sera of patients; to develop and visualize positive plaques we used an anti human Ig antibody alkaline phosphatase conjugated (Cappel, West Chester, Pa.) and the NBT/BCIP kit (Promega, Madison, Wis.) in AP buffer (100 mM Tris pH 9.5, 100 mM NaCl, 5mM $MgCl_2$) according to the manufacturer instructions.

6.1.3. Recombinant DNA Procedures

Reagents and restriction enzymes used were from Sigma (St. Louis, Mo.) and Boehringer (Mannheim, Germany). Standard techniques were used for molecular cloning, single-stranded DNA purification, transformation in *E. coli*, radioactive labelling of probes, colony screening of the *H. pylori* DNA genomic library, Southern blot analysis, PAGE and Western blot analysis.

6.1.4. DNA Sequence Analysis

The DNA fragments were subcloned in Bluescript SK+ (Stratagene, San Diego, Calif.). Single-stranded DNA sequencing was performed by using [$^{33}$P]adATP (New England Nuclear, Boston, Mass.) and the Sequenase kit (U.S. Biochemical Corp., Cleveland, Ohio) according to the manufacturer instructions. The sequence was determined in both strands and each strand was sequenced, on average, twice. Computer sequence analysis was performed using the GCG package.

6.1.5. Recombinant Proteins

MS2 polymerase fusion proteins were produced using the vector pEX34A, a derivative of pEX31. Insert Hp67 (from nucleotide 445 to nucleotide 1402 in FIG. 3), and the EcoRI linkers were cloned in frame into the EcoRi site of the vector. In order to confirm the location of the stop codon, the HpG3' HindIII fragment was cloned in frame into the HindIII site of pEX34A. Recombinant plasmids were transformed in *E. coli* K12 H1 Δtrp. In both cases after induction, a fusion protein of the expected molecular weight was produced. In the case of the EcoRI/EcoRI fragment, the fusion protein obtain after induction was electroeluted to immunize rabbits using standard protocols.

6.2. Results

6.2.1. Screening of an Expression Library and Cloning of HE. pylori hsp

In order to find a serum suitable for the screening of an *H. pylori* DNA expression library, sonicated extracts of *H. pylori* strain CCUG 17874 were tested in Western blot analysis against sera of patients affected by different forms of gastritis. The pattern of antigen recognition by different sera was variable, probably due to differences in the individual immune response as well as to the differences in the antigens expressed by the strains involved in the infection.

Serum N°19 was selected to screen a λgt11 *H. pylori* DNA expression library to identify *H. pylori* specific antigens, expressed in vivo during bacterial growth. Following screening of the library with this serum, many positive clones were isolated and characterized. The nucleotide sequence of one of these, called Hp67, revealed an open-reading frame of 958 base-pairs, coding for a protein with high homology to the hsp6o family of heat-shock proteins, Ellis, Nature 358:191–92 (1992). In order to obtain the entire coding region, we used fragment Hp67 as a probe on Southern blot analysis of *H. pylori* DNA digested with different restriction enzymes. Probe Hp67 recognized two HindIII bands of approximately 800 and 1000 base-pairs, respectively. A genomic *H. pylori* library of HindIII-digested DNA was screened with probe Hp67 and two positive clones (HpG5' and HpG3') of the expected molecular weight were obtained. *E. coli* containing plasmids pHp60G2 (approximately nucleotides 1 to 829) and pHp60G5 (approximately nucleotides 824 to 1838) were deposited with the American Type Culture Collection (ATCC).

6.3. Sequence Analysis

The nucleotide sequence analysis revealed an open-reading frame of 1638 base-pairs, with a putative ribosome binding site 6 base-pairs upstream the starting ATG. FIG. 3 shows the nucleotide and amino acid sequences of *H. pylori* hsp. The putative ribosome-binding and the internal HindIII site are underlined. Cytosine in position 445 and guanine in position 1402 are the first and last nucleotide, respectively, in fragment Hp67. Thymine 1772 was identified as the last putative nucleotide transcribed using an algorithm for the localization of factor-independent terminator regions. The open-reading frame encoded for a protein of 546 amino acids, with a predicted molecular weight of 58.3 KDa and a predicted pI of 5.37. The codon preference of this gene is in agreement with the *H. pylori* codon usage.

The analysis of the hydrophylicity profiles revealed a protein mostly hydrophilic, without a predicted leader peptide or other transmembrane domains. The amino terminal sequence showed 100% homology to the sequence of 30 amino acids determined by Dunn et al., Infect. Immun. 60:1946–51 (1992) on the purified protein and differed by only on reside (Ser42 instead of Lys) from the sequence of 44 amino acids published by Evans et al, Infect. Immun. 60:2125–27 (1992). (Evans et al., 1992). The N-terminal sequence of the mature hsp protein did not contain the starting methionine, indicating that this had been removed after translation.

6.4. Homology with hsp60 Family

The amino acid sequence analysis showed a very strong homology with the family of heat-shock proteins hsp60, whose members are present in every living organism. Based on the degree of homology between hsp60 proteins of different species, *H. pylori* hsp belongs to the subgroup of hsp60 proteins of Gram negative bacteria; however, the degree of homology to the other proteins of the hsp60 family is very high (at least 54% identity).

The homology of the *H. pylori* hsp with other heat shock proteins is fully exemplified in FIG. 3. The *H. pylori* hsp or one or more functional immunostimulatory domains thereof may be conjugated to an oligosaccharide or polysaccharide using the procedures of Example 1 above to produce conjugate compounds according to the invention.

6.5. Expression of Recombinant Proteins and Production of a Polyclonal Antiserum The inserts of clone Hp67 and of clone HpG3' were subcloned in the expression vector pEX34A in order to express these open-reading frames fused to the aminoterminus of the MS2 polymerase. The clones produced recombinant proteins of the expected size and were recognized by the human serum used for the initial screening. The fused protein derived from clone Hp67 was electroeluted and used to immunize rabbits in order to obtain anti-hsp specific polyclonal antisera. The antiserum obtained recognized both fusion proteins, and a protein of 58 KDa on whole-cell extracts of several strains of *H. pylori* tested, including a urease-negative strain and noncytotoxic strains.

Hsp has been shown to be expressed by all the *H. pylori* strains tested and its expression is not associated with the presence of the urease or with the cytotoxicity. The protein recognized by the anti-hsp antiserum was found in the water soluble extracts of *H. pylori* and copurified with the urease subunits. This suggests a weak association of this protein with the outer bacterial membrane. Thus, hsp can be described as urease-associated and surface exposed. The cellular surface localization is surprising as most of the hsp homologous proteins are localized in the cytoplasm or in mitochondria and plastids. The absence of a leader peptide in hsp suggests that this is either exported to the membrane by a peculiar export system, or that the protein is released from the cytoplasm and is passively adsorbed by the bacterial membrane after death of the bacterium.

7. DEPOSIT OF BIOLOGICAL MATERIALS

The following materials were deposited on Dec. 15, 1992 and Jan. 22, 1993 by Biocine Sclavo, S.p.A., the assignee of the present invention, with the American Type Culture Collection (ATCC), 12301 Parklawn Drive, Rockville, Md., phone (301) 231–5519, under the terms of the Budapest Treaty on the International Recognition of the Deposit of Microorganisms for Purposes of Patent Procedure.

ATCC No. 69155 *E. coli* TG1 containing the plasmid pHp60G2

ATCC No. 69156 *E. coli* TG1 containing the plasmid pHp605

These deposits are provided as convenience to those of skill in the art, and are not an admission that a deposit is required under 35 U.S.C. §112 or any equivalent provision in any one of the designated states herein. The nucleic acid sequences of these deposits, as well as the amino acid sequences of the polypeptides encoded thereby, are incorporated herein by reference and should be referred to in the event of any error in the sequences described herein as compared with the sequences of the deposits. A licence may be required to make, use, or sell the deposited materials, and no such license is granted hereby.

What is claimed is:

1. A conjugate compound comprising a portion of at least 11 to 15 amino acid residues of a heat shock protein selected from the group consisting of *M. bovis* BCG GroEL-type 65 kDa heat shock protein and recombinant *M. tuberculosis* DnaK-type 70 kDa heat shock protein, wherein said heat shock protein portion includes at least one immunostimulatory domain, said conjugate compound also comprising at least one capsular oligosaccharide or capsular polysaccharide, or immunogenic portion thereof.

2. A conjugate compound according to claim 1 comprising oligosaccharides of the Meningicocci C (MenC) group and a portion of a heat shock protein.

3. A process for producing a conjugate compound according to claim 1 which comprises covalently bonding said heat shock protein portion including at least one immunostimulatory domain to at least one oligosaccharide or polysaccharide.

4. A method of inducing an immune response comprising administering an immunologically effective amount of a conjugate compound according to claim 1.

5. A conjugate compound comprising a portion of at least 11 to 15 amino acid residues of a heat shock protein selected from the group consisting of *M. bovis* BCG GroEL-type 65 kDa heat shock protein and recombinant *M. tuberculosis* DnaK-type 70 kDa heat shock protein, wherein said heat shock protein portion includes at least one immunostimulatory domain, said conjugate compound also comprising at least one capsular oligosaccharide or capsular polysaccharide, or immunogenic portion thereof from a bacteria selected from the group consisting of Hemophilus, Salmonella, Streptococcus, and Shigella.

6. A conjugate compound comprising at least one heat shock protein from *H. pylori* of about 54–62 kDa, wherein said heat shock protein includes at least one immunostimulatory domain, said conjugate compound also comprising at least one capsular oligosacchalide or capsular polysaccharide, or immunogenic portion thereof.

7. The conjugate compound of claim 6 comprising the heat shock protein from *H. pylori* of about 54–62 kDa, or a portion thereof, wherein said heat shock protein includes at least one immunostimulatory domain, said conjugate compound also comprising at least one capsular oligosaccharide or capsular polysaccharide, or immunogenic portion thereof from a bacteria selected from the group consisting of Hemophilus, Salmonella, Streptococcus, and Shigella.

8. The conjugate compound of claim 6 comprising the heat shock protein from *H. pylori* of about 54–62 kDa, wherein said heat shock protein includes at least one immunostimulatory domain, said conjugate compound also comprising at least one capsular oligosaccharide or immunogenic portion thereof from a bacteria selected from the group consisting of Hemophilus, Salmonella, Streptococcus, and Shigella.

9. A conjugate compound comprising a portion of a heat shock protein selected from the group consisting of *M. bovis* BCG GroEL-type 65 kDa heat shock protein and recombinant *M. tuberculosis* DnaK-type 70 kDa heat shock protein, wherein said portion of said heat shock protein includes an immunostimulatory domain wherein said portion includes one or more of the regions underlined in SEQ ID NO:5 of FIG. 2, said conjugate compound also comprising at least one capsular oligosaccharide or capsular polysaccharide, or immunogenic portion thereof.

10. A conjugate compound comprising a portion of a heat shock protein selected from the group consisting of *M. bovis* BCG GroEL-type 65 kDa heat shock protein and recombinant *M. tuberculosis* DnaK-type 70 kDa heat shock protein, wherein said portion of said heat shock protein includes an immunostimulatory domain wherein said portion includes one or more of the regions underlined in SEQ ID NO:5 of FIG. 2, said conjugate compound also comprising at least one capsular oligosaccharide or capsular polysaccharide, or immunogenic portion thereof from a bacteria selected from the group consisting of Hemophilus, Salmonella, Streptococcus, and Shigella.

11. The conjugate compound of any one of claims 9 or 10 wherein said one of said regions comprises: amino acid residues 27 to 38, amino acid residues 41 to 48, amino acid residues 50 to 58, amino acid residues 60 to 88, amino acid residues 90 to 94, amino acid residues 98 to 107, amino acid residues 109 to 135, amino acid residues 141 to 147, amino acid residues 152 to 189, amino acid residues 202 to 251, or amino acid residues 254 to 272 of SEQ ID NO:5.

* * * * *

SEQUENCE LISTING

<160> NUMBER OF SEQ ID NOS: 7

<210> SEQ ID NO 1
<211> LENGTH: 546
<212> TYPE: PRT
<213> ORGANISM: H. pylori

<400> SEQUENCE: 1

```
Met Ala Lys Glu Ile Lys Phe Ser Asp Ser Ala Arg Asn Leu Leu Phe
1               5                   10                  15

Glu Gly Val Arg Gln Leu His Asp Ala Val Lys Val Thr Met Gly Pro
            20                  25                  30

Arg Gly Arg Asn Val Leu Ile Gln Lys Ser Tyr Gly Ala Pro Ser Ile
        35                  40                  45

Thr Lys Asp Gly Val Ser Val Ala Lys Glu Ile Glu Leu Ser Cys Pro
    50                  55                  60

Val Ala Asn Met Gly Ala Gln Leu Val Lys Glu Val Ala Ser Lys Thr
65                  70                  75                  80

Ala Asp Ala Ala Gly Asp Gly Thr Thr Thr Ala Thr Val Leu Ala Tyr
                85                  90                  95

Ser Ile Phe Lys Glu Gly Leu Arg Asn Ile Thr Ala Gly Ala Asn Pro
            100                 105                 110

Ile Glu Val Lys Arg Gly Met Asp Lys Ala Ala Glu Ala Ile Ile Asn
        115                 120                 125

Glu Leu Lys Lys Ala Ser Lys Lys Val Gly Gly Lys Glu Ile Thr
    130                 135                 140

Gln Val Ala Thr Ile Ser Ala Asn Ser Asp His Asn Ile Gly Lys Leu
145                 150                 155                 160

Ile Ala Asp Ala Met Glu Lys Val Gly Lys Asp Gly Val Ile Thr Val
                165                 170                 175

Glu Glu Ala Lys Gly Ile Glu Asp Leu Asp Val Val Glu Gly Met
            180                 185                 190

Gln Phe Asp Arg Gly Tyr Leu Ser Pro Tyr Phe Val Thr Asn Ala Glu
        195                 200                 205

Lys Met Thr Ala Gln Leu Asp Asn Ala Tyr Ile Leu Leu Thr Asp Lys
    210                 215                 220

Lys Ile Ser Ser Met Lys Asp Ile Leu Pro Leu Leu Glu Lys Thr Met
225                 230                 235                 240

Lys Glu Gly Lys Pro Leu Leu Ile Ile Ala Glu Asp Ile Glu Gly Glu
                245                 250                 255

Ala Leu Thr Thr Leu Val Val Asn Lys Leu Arg Gly Val Leu Asn Ile
            260                 265                 270

Ala Ala Val Lys Ala Pro Gly Phe Gly Asp Arg Arg Lys Glu Met Leu
        275                 280                 285

Lys Asp Ile Ala Ile Leu Thr Gly Gly Gln Val Ile Ser Glu Glu Leu
    290                 295                 300

Gly Leu Ser Leu Glu Asn Ala Glu Val Glu Phe Leu Gly Lys Ala Gly
305                 310                 315                 320

Arg Ile Val Ile Asp Lys Asp Asn Thr Thr Ile Val Asp Gly Lys Gly
                325                 330                 335

His Ser Asp Asp Val Lys Asp Arg Val Ala Gln Ile Lys Thr Gln Ile
            340                 345                 350

Ala Ser Thr Thr Ser Asp Tyr Asp Lys Glu Lys Leu Gln Glu Arg Leu
```

```
                355                 360                 365
Ala Lys Leu Ser Gly Gly Val Ala Val Ile Lys Val Gly Ala Ala Ser
        370                 375                 380

Glu Val Glu Met Lys Glu Lys Lys Asp Arg Val Asp Asp Ala Leu Ser
385                 390                 395                 400

Ala Thr Lys Ala Ala Val Glu Glu Gly Ile Val Ile Gly Gly Gly Ala
                405                 410                 415

Ala Leu Ile Arg Ala Ala Gln Lys Val His Leu Asn Leu His Asp Asp
            420                 425                 430

Glu Lys Val Gly Tyr Glu Ile Ile Met Arg Ala Ile Lys Ala Pro Leu
        435                 440                 445

Ala Gln Ile Ala Ile Asn Ala Gly Tyr Asp Gly Gly Val Val Val Asn
        450                 455                 460

Glu Val Glu Lys His Glu Gly His Phe Gly Phe Asn Ala Ser Asn Gly
465                 470                 475                 480

Lys Tyr Val Asp Met Phe Lys Glu Gly Ile Ile Asp Pro Leu Lys Val
                485                 490                 495

Glu Arg Ile Ala Leu Gln Asn Ala Val Ser Val Ser Ser Leu Leu Leu
            500                 505                 510

Thr Thr Glu Ala Thr Val His Glu Ile Lys Glu Glu Lys Ala Thr Pro
        515                 520                 525

Ala Met Pro Asp Met Gly Gly Met Gly Gly Met Gly Gly Met Gly Gly
        530                 535                 540

Met Met
545

<210> SEQ ID NO 2
<211> LENGTH: 202
<212> TYPE: PRT
<213> ORGANISM: P. aeruginosa

<400> SEQUENCE: 2

Met Ala Val Gly Lys Lys Met Leu Val Asn Val Ala Ala Leu Lys Val
1               5                   10                  15

Leu Asp Phe Thr Lys Asp Lys Phe Glu Asp Arg Pro Thr Gln Ala Val
            20                  25                  30

Asn Lys Ala Val Ala Ala Met Met Asp Leu Ile Pro Thr Val Val Ala
        35                  40                  45

Gln Glu Leu Ala Pro Trp Arg Asp Thr Lys Ala Ala Gly Glu Ser Gln
    50                  55                  60

Ile Glu Glu Gly Ser Leu Asn Ser Asn Lys Pro Asp Thr Ala Glu Ser
65                  70                  75                  80

Pro Leu Leu Val Asn Ile Arg Glu Met Val Ala Val Ala Ala Arg Val
                85                  90                  95

Val Ala Asn Met Ile Val Lys Ala Gln Thr Val Gly Thr Leu His Pro
            100                 105                 110

Lys Val Asn Glu Ile Ala Val Gln Ala Ile Glu Ala Leu Arg Lys Glu
        115                 120                 125

Glu Arg Thr Ala Pro Glu His Arg Val Pro Val Val Leu Ala Ile Glu
    130                 135                 140

Gly Lys Gly Asp Asn Glu Glu Gln Asn Ile Ala Leu Leu Arg Val Glu
145                 150                 155                 160

Ser Val Arg Ala Asp Glu Pro Ser Asp Lys Lys Gln Gly Ser Asn Tyr
                165                 170                 175
```

-continued

```
Ala Thr Val Gly Ile Glu Met Leu Ala Thr S er Ala Ala Ile Gly Gly
            180                 185                 190

Met Ile Met Ala Val Asp Gly Gly Pro Asp
        195                 200

<210> SEQ ID NO 3
<211> LENGTH: 218
<212> TYPE: PRT
<213> ORGANISM: C. trachomatis

<400> SEQUENCE: 3

Met Val Asn Tyr Asn Glu Glu Lys Lys Ile G ln Lys Lys Thr Ala Glu
1               5                   10                  15

Leu Lys His Val Asp Phe Ser Gln Val Thr V al Ala Asp Lys His Glu
            20                  25                  30

Met Lys Glu Ala Tyr Thr Val Met Asp Leu I le Val Lys Val Val Val
        35                  40                  45

Asp Gln Ile Ile Pro Gln His His Lys Ala A sn Ala Glu Asn Glu Asn
    50                  55                  60

Ser Phe Thr Val Asn Asn Ser Ala Pro Thr G ln Glu Cys Val Glu Asp
65                  70                  75                  80

Leu Val Ile Tyr Gly Ile Phe Ile Gln Gln V al Ala Glu Ser Arg Ala
                85                  90                  95

Arg Ile Gly Phe Arg Val Cys Ala Glu Leu M et Lys Asn Leu Ala Met
            100                 105                 110

Lys Lys Val Ile Val Ser Glu Asp Glu Met G lu Lys Glu Ala Leu Glu
        115                 120                 125

Ala Cys Glu Ser Lys Glu Asp Ser Ser Arg T hr Ile Gln His Ile Leu
    130                 135                 140

Pro Thr Cys Ile Pro Thr Leu Glu Ala Phe P ro Met Leu Thr Asn Glu
145                 150                 155                 160

Gln Ile Ala Arg Val Leu Lys Leu Ser Lys A la Lys Glu Ala Ile Ile
                165                 170                 175

Phe Gln Gln Met Ser Arg Ser Ala Asn Glu T yr Asp Leu Arg Asp Ala
            180                 185                 190

Thr Leu Glu Ala Leu Ala Thr Ser Glu Ser A la Val Ala Gly Leu Ile
        195                 200                 205

Ala Pro Pro Ala Ala Pro Ala Asp Tyr
    210                 215

<210> SEQ ID NO 4
<211> LENGTH: 274
<212> TYPE: PRT
<213> ORGANISM: M. leprae

<400> SEQUENCE: 4

Val Pro Gly Arg Asp Gly Glu Thr Gln Pro A la Ser Cys Gly Arg Pro
1               5                   10                  15

Ser Arg Ala Leu His Pro Ala Ser Val Ser A sn Gly Gly Cys Arg His
            20                  25                  30

Pro Val Thr Leu Ala Ser Phe Leu Ile Arg A rg Asn His Phe Ala Thr
        35                  40                  45

Ala Tyr Asp Glu Glu Arg Gly Glu Arg Leu A sn Ser Ala Leu Lys Val
    50                  55                  60

Leu Glu Lys Trp Thr Asn Ile Glu Asp Tyr G lu Lys Ile Glu Lys Asp
65                  70                  75                  80
```

-continued

```
Val Gln Ala Leu Val Val Ala Leu Gly Leu Ile Glu Val Asp Lys Val
                85                  90                  95

Thr Glu Thr Leu Asp Ala Glu Thr Gln Ala Ala Thr Ala Gly Gln
            100                 105                 110

Ser Asp Glu Asp Asn Glu Ser Asn Thr Phe Gly Leu Gln Glu Leu Thr
            115                 120                 125

Arg Lys Ile Gly Asp Arg Gln Glu Val Glu Pro Val Ser Ser Val
            130                 135             140

Thr Val Leu Val Ile Gln Ala Ser Val Ser Ile Thr Phe Lys Ser Val
145                 150                 155                 160

Ala Gln Met Ala Val Thr Thr Asp Leu Ser Leu Arg Lys Val Met Thr
                165                 170                 175

Glu Glu Ala Asp Thr Ala Ile Ala Gly Arg Glu Glu Asn Ser Asp Arg
                180                 185                 190

Ala Ala Thr Leu Arg His Ile Glu Val Arg Asn Ala Ala Val Thr Leu
                195                 200                 205

Gln Pro Ala Leu Asp Lys Lys Thr Gly Ala Thr Ala Asn Val Lys Val
            210                 215                 220

Leu Glu Lys Phe Ser Met Glu Pro Ala Glu Lys Arg Asn Leu Ser Val
225                 230                 235                 240

Gly His Leu Ala Thr Glu Glu Leu Leu Ala Val Ala Val Thr Ser Ala
                245                 250                 255

Ile Ala Gly Phe Val Ala Asp Lys Pro Lys Thr Ala Ser Asp Pro Thr
                260                 265                 270

Asp Phe

<210> SEQ ID NO 5
<211> LENGTH: 278
<212> TYPE: PRT
<213> ORGANISM: Homo sapiens

<400> SEQUENCE: 5

Met Leu Arg Leu Pro Thr Val Phe Arg Gln Met Arg Pro Val Ser Arg
1               5                   10                  15

Val Leu Ala Pro His Leu Thr Arg Ala Tyr Asp Val Gly Ala Asp Ala
                20                  25                  30

Met Leu Gln Asp Leu Ala Ala Lys Thr Ile Glu Gln Trp Ser Lys Val
            35                  40                  45

Thr Ser Asp Glu Asp Lys Tyr Lys Ile Lys Gln Asp Asn Asn Asn Glu
        50                  55                  60

Glu Arg Ala Phe Glu Lys Ser Val Ile Arg Val Met Leu Val Asp
65                  70                  75                  80

Val Ala Gln Pro Thr Thr Pro Ala Gly Lys Glu Asn Ile Ser Lys Arg
                85                  90                  95

Lys Lys Asp Gly Thr Leu Asn Glu Ile Ile Lys Ile Ile Asn Thr Ser
            100                 105                 110

Lys Gly Lys Cys Glu Phe Gln Asp Val Ser Glu Ile Gln Ser Val Ala
            115                 120                 125

Ile Ala Asn Ala His Arg Val Val Asp Ser Leu Arg Lys Val Gly Gln
            130                 135                 140

Val Val Asn Asn Gln Met Ala Ala Phe Gly Gly Thr Asn Asp Val Gln
145                 150                 155                 160

Pro His Asp Val Glu Val Ile Val Thr Asp Ala Met Leu Leu Lys Asp
                165                 170                 175
```

-continued

```
Lys Ala Gln Ile Glu Lys Ile Gln Glu Ile G lu Leu Asp Val Glu Glu
            180                 185                 190

Asn Asp Leu Gly Thr Asp Asn Val Thr Asn A rg Leu Cys Leu Cys Ile
            195                 200                 205

Pro Ala Leu Asp Ser Thr Pro Ala Asn Glu G ln Ile Ile Lys Thr Leu
            210                 215                 220

Ile Ala Met Thr Lys Val Glu Ser Leu Ile G lu Lys Ile Met Gln Ser
225                 230                 235                 240

Ser Ser Glu Val Tyr Asp Met Ala Asp Phe A sn Val Glu Lys Thr Val
                    245                 250                 255

Thr Leu Asp Ala Gly Ala Thr Ala Val Val T hr Pro Lys Glu Lys Asp
            260                 265                 270

Gly Gly Ala Gly Met Phe
            275

<210> SEQ ID NO 6
<211> LENGTH: 1838
<212> TYPE: DNA
<213> ORGANISM: H. pylori
<220> FEATURE:
<221> NAME/KEY: CDS
<222> LOCATION: (58)..(1695)
<223> OTHER INFORMATION:

<400> SEQUENCE: 6
aagcttgctg tcatgatcac aaaaaacact aaaaaacatt attattaagg a tacaaa           57 atg gca aaa gaa atc aaa ttt tca gat agt g cg aga aac ctt tta ttt       105
Met Ala Lys Glu Ile Lys Phe Ser Asp Ser A la Arg Asn Leu Leu Phe
1               5                  10                   15 gaa ggc gtg agg caa ctc cat gac gct gtc a aa gta acc atg ggg cca       153
Glu Gly Val Arg Gln Leu His Asp Ala Val L ys Val Thr Met Gly Pro
            20                  25                   30 aga ggc agg aat gta ttg atc caa aaa agc t at ggc gct cca agc atc       201
Arg Gly Arg Asn Val Leu Ile Gln Lys Ser T yr Gly Ala Pro Ser Ile
        35                  40                   45 acc aaa gac ggc gtg agc gtg gct aaa gag a tt gaa tta agt tgc cca       249
Thr Lys Asp Gly Val Ser Val Ala Lys Glu I le Glu Leu Ser Cys Pro
    50                  55                   60 gta gct aac atg ggc gct caa ctc gtt aaa g aa gta gcg agc aaa acc       297
Val Ala Asn Met Gly Ala Gln Leu Val Lys G lu Val Ala Ser Lys Thr
65              70                   75                   80 gct gat gct gcc ggc gat ggc acg acc aca g cg acc gtg cta gct tat       345
Ala Asp Ala Ala Gly Asp Gly Thr Thr Thr A la Thr Val Leu Ala Tyr
                85                   90                   95 agc att ttt aaa gaa ggt ttg agg aat atc a cg gct ggg gct aac cct       393
Ser Ile Phe Lys Glu Gly Leu Arg Asn Ile T hr Ala Gly Ala Asn Pro
            100                 105                 110 att gaa gtg aaa cga ggc atg gat aaa gct g ct gaa gcg atc att aat       441
Ile Glu Val Lys Arg Gly Met Asp Lys Ala A la Glu Ala Ile Ile Asn
        115                 120                 125 gag ctt aaa aaa gcg agc aaa aaa gta ggc g gt aaa gaa gaa atc acc       489
Glu Leu Lys Lys Ala Ser Lys Lys Val Gly G ly Lys Glu Glu Ile Thr
    130                 135                 140 caa gtg gcg acc att tct gca aac tcc gat c ac aat atc ggg aaa ctc       537
Gln Val Ala Thr Ile Ser Ala Asn Ser Asp H is Asn Ile Gly Lys Leu
145                 150                 155                 160 atc gct gac gct atg gaa aaa gtg ggt aaa g ac ggc gtg atc acc gtt       585
Ile Ala Asp Ala Met Glu Lys Val Gly Lys A sp Gly Val Ile Thr Val
                165                 170                 175
```

-continued

| | |
|---|---|
| gag gaa gct aag ggc att gaa gat gaa ttg g at gtc gta gaa ggc atg<br>Glu Glu Ala Lys Gly Ile Glu Asp Glu Leu A sp Val Val Glu Gly Met<br>180           185             190 | 633 |
| caa ttt gat aga ggc tac ctc tcc cct tat t tt gta acg aac gct gag<br>Gln Phe Asp Arg Gly Tyr Leu Ser Pro Tyr P he Val Thr Asn Ala Glu<br>195           200             205 | 681 |
| aaa atg acc gct caa ttg gat aat gct tac a tc ctt tta acg gat aaa<br>Lys Met Thr Ala Gln Leu Asp Asn Ala Tyr I le Leu Leu Thr Asp Lys<br>210           215             220 | 729 |
| aaa atc tct agc atg aaa gac att ctc ccg c ta cta gaa aaa acc atg<br>Lys Ile Ser Ser Met Lys Asp Ile Leu Pro L eu Leu Glu Lys Thr Met<br>225           230             235           240 | 777 |
| aaa gag ggc aaa ccg ctt tta atc atc gct g aa gac att gag ggc gaa<br>Lys Glu Gly Lys Pro Leu Leu Ile Ile Ala G lu Asp Ile Glu Gly Glu<br>          245             250             255 | 825 |
| gct tta acg act cta gtg gtg aat aaa tta a ga ggc gtg ttg aat atc<br>Ala Leu Thr Thr Leu Val Val Asn Lys Leu A rg Gly Val Leu Asn Ile<br>          260             265             270 | 873 |
| gca gcg gtt aaa gct cca ggc ttt ggg gac a ga aga aaa gaa atg ctc<br>Ala Ala Val Lys Ala Pro Gly Phe Gly Asp A rg Arg Lys Glu Met Leu<br>          275             280             285 | 921 |
| aaa gac atc gct att tta acc ggc ggt caa g tc att agc gaa gaa ttg<br>Lys Asp Ile Ala Ile Leu Thr Gly Gly Gln V al Ile Ser Glu Glu Leu<br>290           295             300 | 969 |
| ggc ttg agt cta gaa aac gct gaa gtg gag t tt tta ggc aaa gct gga<br>Gly Leu Ser Leu Glu Asn Ala Glu Val Glu P he Leu Gly Lys Ala Gly<br>305           310             315           320 | 1017 |
| agg att gtg att gac aaa gac aac acc acg a tc gta gat ggc aaa ggc<br>Arg Ile Val Ile Asp Lys Asp Asn Thr Thr I le Val Asp Gly Lys Gly<br>          325             330             335 | 1065 |
| cat agc gat gat gtt aaa gac aga gtc gcg c ag atc aaa acc caa att<br>His Ser Asp Asp Val Lys Asp Arg Val Ala G ln Ile Lys Thr Gln Ile<br>          340             345             350 | 1113 |
| gca agt acg aca agc gat tat gac aaa gaa a aa ttg caa gaa aga ttg<br>Ala Ser Thr Thr Ser Asp Tyr Asp Lys Glu L ys Leu Gln Glu Arg Leu<br>          355             360             365 | 1161 |
| gct aaa ctc tct ggc ggt gtg gct gtg att a aa gtg ggc gct gcg agt<br>Ala Lys Leu Ser Gly Gly Val Ala Val Ile L ys Val Gly Ala Ala Ser<br>370           375             380 | 1209 |
| gaa gtg gaa atg aaa gag aaa aaa gac cgg g tg gat gac gcg ttg agc<br>Glu Val Glu Met Lys Glu Lys Lys Asp Arg V al Asp Asp Ala Leu Ser<br>385           390             395           400 | 1257 |
| gcg act aaa gcg gcg gtt gaa gaa ggc att g tg att ggt ggc ggt gcg<br>Ala Thr Lys Ala Ala Val Glu Glu Gly Ile V al Ile Gly Gly Gly Ala<br>          405             410             415 | 1305 |
| gct ctc att cgc gcg gct caa aaa gtg cat t tg aat ttg cac gat gat<br>Ala Leu Ile Arg Ala Ala Gln Lys Val His L eu Asn Leu His Asp Asp<br>          420             425             430 | 1353 |
| gaa aaa gtg ggc tat gaa atc atc atg cgc g cc att aaa gcc cca tta<br>Glu Lys Val Gly Tyr Glu Ile Ile Met Arg A la Ile Lys Ala Pro Leu<br>          435             440             445 | 1401 |
| gct caa atc gct atc aac gct ggt tat gat g gc ggt gtg gtc gtg aat<br>Ala Gln Ile Ala Ile Asn Ala Gly Tyr Asp G ly Gly Val Val Val Asn<br>450           455             460 | 1449 |
| gaa gta gaa aaa cac gaa ggg cat ttt ggt t tt aac gct agc aat ggc<br>Glu Val Glu Lys His Glu Gly His Phe Gly P he Asn Ala Ser Asn Gly<br>465           470             475           480 | 1497 |
| aag tat gtg gat atg ttt aaa gaa ggc att a tt gac ccc tta aaa gta<br>Lys Tyr Val Asp Met Phe Lys Glu Gly Ile I le Asp Pro Leu Lys Val<br>          485             490             495 | 1545 |

```
gaa agg atc gct cta caa aat gcg gtt tcg g tt tca agc ctg ctt tta      1593
Glu Arg Ile Ala Leu Gln Asn Ala Val Ser V al Ser Ser Leu Leu Leu
            500                 505                 510 acc aca gaa gcc acc gtg cat gaa atc aaa g aa gaa aaa gcg act ccg      1641
Thr Thr Glu Ala Thr Val His Glu Ile Lys G lu Glu Lys Ala Thr Pro
    515                 520                 525 gca atg cct gat atg ggt ggc atg ggt a tg gga ggc atg ggc ggc          1689
Ala Met Pro Asp Met Gly Gly Met Gly Gly M et Gly Gly Met Gly Gly
530                 535                 540 atg atg taagcccgct tgcttttag tataatctgc ttttaaaatc c cttctctaa        1745
Met Met
545 atccccccct ttctaaaatc tcttttttgg gggggtgctt tgataaaacc g ctcgcttgt    1805 aaaaacatgc aacaaaaaat ctctgttaag ctt                                  1838

<210> SEQ ID NO 7
<211> LENGTH: 546
<212> TYPE: PRT
<213> ORGANISM: H. pylori

<400> SEQUENCE: 7

Met Ala Lys Glu Ile Lys Phe Ser Asp Ser A la Arg Asn Leu Leu Phe
1               5                   10                  15

Glu Gly Val Arg Gln Leu His Asp Ala Val L ys Val Thr Met Gly Pro
            20                  25                  30

Arg Gly Arg Asn Val Leu Ile Gln Lys Ser T yr Gly Ala Pro Ser Ile
        35                  40                  45

Thr Lys Asp Gly Val Ser Val Ala Lys Glu I le Glu Leu Ser Cys Pro
    50                  55                  60

Val Ala Asn Met Gly Ala Gln Leu Val Lys G lu Val Ala Ser Lys Thr
65                  70                  75                  80

Ala Asp Ala Ala Gly Asp Gly Thr Thr Thr A la Thr Val Leu Ala Tyr
                85                  90                  95

Ser Ile Phe Lys Glu Gly Leu Arg Asn Ile T hr Ala Gly Ala Asn Pro
            100                 105                 110

Ile Glu Val Lys Arg Gly Met Asp Lys Ala A la Glu Ala Ile Ile Asn
        115                 120                 125

Glu Leu Lys Lys Ala Ser Lys Lys Val Gly G ly Lys Glu Glu Ile Thr
    130                 135                 140

Gln Val Ala Thr Ile Ser Ala Asn Ser Asp H is Asn Ile Gly Lys Leu
145                 150                 155                 160

Ile Ala Asp Ala Met Glu Lys Val Gly Lys A sp Gly Val Ile Thr Val
                165                 170                 175

Glu Glu Ala Lys Gly Ile Glu Asp Glu Leu A sp Val Val Glu Gly Met
            180                 185                 190

Gln Phe Asp Arg Gly Tyr Leu Ser Pro Tyr P he Val Thr Asn Ala Glu
        195                 200                 205

Lys Met Thr Ala Gln Leu Asp Asn Ala Tyr I le Leu Leu Thr Asp Lys
    210                 215                 220

Lys Ile Ser Ser Met Lys Asp Ile Leu Pro L eu Leu Glu Lys Thr Met
225                 230                 235                 240

Lys Glu Gly Lys Pro Leu Leu Ile Ile Ala G lu Asp Ile Glu Gly Glu
                245                 250                 255

Ala Leu Thr Thr Leu Val Val Asn Lys Leu A rg Gly Val Leu Asn Ile
            260                 265                 270
```

```
Ala Ala Val Lys Ala Pro Gly Phe Gly Asp Arg Arg Lys Glu Met Leu
            275                 280                 285
Lys Asp Ile Ala Ile Leu Thr Gly Gly Gln Val Ile Ser Glu Glu Leu
            290                 295                 300
Gly Leu Ser Leu Glu Asn Ala Glu Val Glu Phe Leu Gly Lys Ala Gly
305                 310                 315                 320
Arg Ile Val Ile Asp Lys Asp Asn Thr Thr Ile Val Asp Gly Lys Gly
                    325                 330                 335
His Ser Asp Asp Val Lys Asp Arg Val Ala Gln Ile Lys Thr Gln Ile
                340                 345                 350
Ala Ser Thr Thr Ser Asp Tyr Asp Lys Glu Lys Leu Gln Glu Arg Leu
            355                 360                 365
Ala Lys Leu Ser Gly Gly Val Ala Val Ile Lys Val Gly Ala Ala Ser
            370                 375                 380
Glu Val Glu Met Lys Glu Lys Lys Asp Arg Val Asp Asp Ala Leu Ser
385                 390                 395                 400
Ala Thr Lys Ala Ala Val Glu Glu Gly Ile Val Ile Gly Gly Gly Ala
                405                 410                 415
Ala Leu Ile Arg Ala Ala Gln Lys Val His Leu Asn Leu His Asp Asp
                420                 425                 430
Glu Lys Val Gly Tyr Glu Ile Ile Met Arg Ala Ile Lys Ala Pro Leu
            435                 440                 445
Ala Gln Ile Ala Ile Asn Ala Gly Tyr Asp Gly Gly Val Val Val Asn
            450                 455                 460
Glu Val Glu Lys His Glu Gly His Phe Gly Phe Asn Ala Ser Asn Gly
465                 470                 475                 480
Lys Tyr Val Asp Met Phe Lys Glu Gly Ile Ile Asp Pro Leu Lys Val
                485                 490                 495
Glu Arg Ile Ala Leu Gln Asn Ala Val Ser Val Ser Ser Leu Leu Leu
                500                 505                 510
Thr Thr Glu Ala Thr Val His Glu Ile Lys Glu Glu Lys Ala Thr Pro
            515                 520                 525
Ala Met Pro Asp Met Gly Gly Met Gly Gly Met Gly Gly Met Gly Gly
            530                 535                 540
Met Met
545
```